(12) United States Patent
Kjeldsen et al.

(10) Patent No.: US 8,883,449 B2
(45) Date of Patent: Nov. 11, 2014

(54) SINGLE-CHAIN INSULIN

(75) Inventors: Thomas Børglum Kjeldsen, Virum (DK); Morten Schlein, Copenhagen (DK); Anders Robert Sørensen, Herlev (DK); Peter Madsen, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/251,901

(22) Filed: Oct. 15, 2008

(65) Prior Publication Data

US 2009/0170750 A1    Jul. 2, 2009

Related U.S. Application Data

(63) Continuation of application No. 11/439,897, filed on May 24, 2006, now abandoned, which is a continuation of application No. PCT/DK2004/000843, filed on Dec. 3, 2004.

(60) Provisional application No. 60/530,106, filed on Dec. 16, 2003.

(30) Foreign Application Priority Data

Dec. 3, 2003    (DK) ................................. 2003 01786

(51) Int. Cl.
| | |
|---|---|
| *C07K 14/62* | (2006.01) |
| *A61K 36/28* | (2006.01) |
| *C12N 5/10* | (2006.01) |
| *C12N 1/21* | (2006.01) |
| *C12N 15/17* | (2006.01) |
| *C12N 15/63* | (2006.01) |
| *A61K 38/00* | (2006.01) |

(52) U.S. Cl.
CPC    *C07K 14/62* (2013.01); *A61K 38/00* (2013.01)
USPC ....... 435/69.4; 435/320.1; 435/325; 435/243; 514/5.9; 530/303

(58) Field of Classification Search
CPC .................................................... A61K 38/28
See application file for complete search history.

(56) References Cited

U.S. PATENT DOCUMENTS

| | | | |
|---|---|---|---|
| 4,916,212 | A | 4/1990 | Markussen et al. |
| 5,008,241 | A | 4/1991 | Markussen |
| 6,534,288 | B1 | 3/2003 | Habermann et al. |
| 6,630,348 | B1 | 10/2003 | Lee et al. |

FOREIGN PATENT DOCUMENTS

| | | |
|---|---|---|
| CN | 1414974 | 4/2003 |
| EP | 427296 | 5/1984 |
| EP | 518587 | 6/1991 |
| EP | 741188 | 5/1995 |
| EP | 1193272 | 10/2000 |
| EP | 1193272 | 4/2002 |
| JP | 61-1389 | 1/1986 |
| JP | 2002-320490 | 11/2002 |
| JP | 2003/511018 | 3/2003 |
| JP | 2003/518945 | 6/2003 |
| KR | 2003-0063266 | 7/2003 |
| WO | WO 95/16708 | 6/1995 |
| WO | WO 96/34882 | 11/1996 |
| WO | WO 99/21573 | 5/1999 |
| WO | WO 01/25278 | 4/2001 |
| WO | WO 01/49742 | 7/2001 |
| WO | WO 01/49870 | 7/2001 |
| WO | WO 02/079250 | * 10/2002 |

OTHER PUBLICATIONS

Liu, M. et al.., J. of Biol. Chem., vol. 278(17), pp. 14798-14805, 2003.
Marcussen, J. et al., Protein Engineering, vol. 1 (3), pp. 205-213, 1987.
Marcussen, J. et al., Protein Engineering, vol. 1 (3), pp. 215-223, 1987.
Marcussen, J. et al., Protein Engineering, vol. 2 (2), pp. 157-166, 1988.
Bullesbach, E. E., Chem. Pep. Proteins, vol. 2, pp. 23-28, 1984.
Lee, H. C. et al., Nature, vol. 408, pp. 438-488, 2000.
Huang, Y. et al., "The Relationship Between the Connecting Peptide of Recombined Single Chain Insulin and its Biological Function", Science in China (Series C), 2001, vol. 44, No. 6, pp. 593-600.
English language abstract of KR 2003-0063266.

* cited by examiner

*Primary Examiner* — Christine J Saoud
(74) *Attorney, Agent, or Firm* — Jianjie Hu

(57) ABSTRACT

The present invention is related to single-chain insulin having insulin activity comprising a B- and an A-chain or a modified B- and A-chain connected by a connecting peptide of from 6-11 amino acids. The single-chain insulins will have biological insulin activity and an IGF-1 receptor affinity similar to or lower than that of human insulin and a high physical stability. The single-chain insulin may contain at least one basic amino acid residues in the connecting peptide. The single-chain insulins may also be acylated in one or more Lys residues.

18 Claims, 3 Drawing Sheets

Disappearance of SCI-112 after S.C. administration in pig AnP

N= 6 pigs

| NNC 0100-0000- | conc | Zn/hex | isotonic | Phe/Cre | albumin | phosphate | inj.vol |
|---|---|---|---|---|---|---|---|
| SCI-112 | 600 µM | 3 | Glycerol 1.6 % | 16 mM | 0 | 0 pH 5.0 | 100 µL |

Disapperance of SCI after S:C: administration in pig
Mean +/- SEM

SINGLE-CHAIN INSULIN

FIELD OF THE INVENTION

The present invention is related to single-chain insulins which have insulin activity and can be used for the treatment of diabetes. The single-chain insulins have a high physical stability and a low tendency to fibrillation and will be soluble at neutral pH. The present invention is also related to a DNA sequence encoding the single-chain insulins, a method for their production and pharmaceutical compositions containing the single-chain insulins.

BACKGROUND OF THE INVENTION

Insulin is a polypeptide hormone secreted by β-cells of the pancreas and consists of two polypeptide chains, A and B, which are linked by two inter-chain disulphide bridges. Further-more, the A-chain features one intra-chain disulphide bridge.

The hormone is synthesized as a single-chain precursor proinsulin (preproinsulin) consisting of a prepeptide of 24 amino acid followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains to form the two-chain insulin molecule. Insulin is essential in maintaining normal metabolic regulation.

The two chain structure of insulin allows insulin to undertake multiple conformations, and several findings have indicated that insulin has the propensity to considerable conformational change and that restrictions in the potential for such change considerably decrease the affinity of the insulin receptor for ligands. Proinsulin has a 100 fold lower affinity for the insulin receptor than native insulin. Blocking of the amino acid residue A1 in insulin also results in poor receptor binding, consistent with the dogma that a free N-terminal of the A-chain and free C-terminal of the B-chain of insulin are important for binding to the insulin receptor.

The inherited physical and chemical stability of the insulin molecule is a basic condition for insulin therapy of diabetes mellitus. These basic properties are fundamental for insulin formulation and for applicable insulin administration methods, as well as for shelf-life and storage conditions of pharmaceutical preparations. Use of solutions in administration of insulin exposes the molecule to a combination of factors, e.g. elevated temperature, variable air-liquid-solid interphases as well as shear forces, which may result in irreversible conformation changes e.g. fibrillation. This is particularly relevant for insulin solutions in infusion pumps, either worn externally or implanted, which exposes the molecule to a combination of these factors as well as shear forces from the movement of the pump for extended periods of time. Consequently, fibrillation is especially a concern when using infusion pumps as insulin delivery system. Moreover, the solubility of insulin is influenced by multiple factors and shows clear reduction in the pH range from 4.2 and 6.6. The pH precipitation zone generally imposes limitations for formulation, but has also been used deliberately in development and formulation of certain analogues.

Thus, the stability and solubility properties of insulin are important underlying aspects for current insulin therapy. The present invention is addressed to these issues by providing stable, single-chain insulin analogues by introduction of a C-peptide between the B- and A-chain to decrease molecular flexibility and concomitantly reduce the fibrillation propensity and limit or modify the pH precipitation zone.

Single-chain insulins with insulin activity are disclosed in EP 1,193,272. These single-chain insulins have a modified C-peptide of 5-18 amino acids and are reported to have up to 42% insulin activity. EP 1,193,272 discloses the following modified C-peptides connecting B30 with A21: Gly-Gly-Gly-Pro-Gly-Lys-Arg(SEQ ID NO:1), Arg-Arg-Gly-Pro-Gly-Gly-Gly(SEQ ID NO:2), Gly-Gly-Gly-Gly-Gly-Lys-Arg(SEQ ID NO:3), Arg-Arg-Gly-Gly-Gly-Gly-Gly(SEQ ID NO:4), Gly-Gly-Ala-Pro-Gly-Asp-Val-Lys-Arg(SEQ ID NO:5), Arg-Arg-Ala-Pro-Gly-Asp-Val-Gly-Gly(SEQ ID NO:6), Gly-Gly-Tyr-Pro-Gly-Asp-Val-Lys-Arg(SEQ ID NO:7), Arg-Arg-Tyr-Pro-Gly-Asp-Val-Gly-Gly(SEQ ID NO:8), Gly-Gly-His-Pro-Gly-Asp-Val-Lys-Arg(SEQ ID NO:9), and Arg-Arg-His-Pro-Gly-Asp-Val-Gly-Gly(SEQ ID NO:10). EP 741,188 discloses single-chain insulins with a modified C-peptide having from 10-14 amino acids residues and having from 14 to 34% insulin activity and having the following connecting peptides Gln-Pro-Leu-Ala-Leu-Glu-Gly-Ser-Leu-Gln-Lys-Arg(SEQ ID NO:11) and Gly-Tyr-Gly-Ser-Ser-Ser-Arg-Arg-Ala-Pro-Gln-Thr(SEQ ID NO:12). WO 95/16708 discloses single-chain insulins with a connecting peptide of 1-15 amino acid residues and with no Lys or Arg as the C-terminal amino acid residue in the connecting peptide. WO 95/16708 discloses the following C-peptide sequences Gly-Tyr-Gly-Ser-Ser-Ser-Arg-Arg-Ala-Pro-Gln-Thr(SEQ ID NO:13) and Gly-Tyr-Gly-Ser-Ser-Ser-Ala-Ala-Ala-Pro-Gln-Thr(SEQ ID NO:14). These single-chain insulins are reported to have insulin activity but also a fairly high affinity to the IGF-1 receptor.

It is the object of the present invention to provide single-chain insulins which have improved properties over the known compounds both with respect to insulin activity, physical stability and solubility as well as pharmacokinetic e.g. a protracted or rapid action profile. A still further object of this invention is to provide a method for making the single-chain insulins and pharmaceutical compositions containing such compounds.

SUMMARY OF THE INVENTION

In one aspect the present invention is related to single-chain insulin having biological insulin activity and comprising the B- and the A-chain of human insulin or analogues or derivatives thereof connected by a connecting peptide, wherein the connecting peptide has from 5-11 amino acid residues and does not contain two adjacent basic amino acid residues and wherein the single-chain insulin has an affinity to the human insulin receptor of at least about 20% of that of human insulin if the single-chain insulin molecule is not chemically modified by acylation.

In another aspect the present invention is related to single-chain insulin having biological insulin activity and comprising the B- and the A-chain of human insulin or analogues or derivatives thereof connected by a connecting peptide, wherein the connecting peptide has from 5-11 amino acid residues provided that if the connecting peptide contains two adjacent basic amino acid residues then at least one of the natural amino acid residues in the B and/or A chain is substituted with another codable amino acid residue or at least one lysine residue in the A-chain, in the B-chain or in the connecting peptide has been chemically modified by acylation or the connecting peptide is not one of the following sequences Gly-Gly-Gly-Pro-Gly-Lys-Arg(SEQ ID NO:1), Arg-Arg-Gly-Pro-Gly-Gly-Gly(SEQ ID NO:2), Gly-Gly-Gly-Gly-Gly-Lys-Arg(SEQ ID NO:3), Arg-Arg-Gly-Gly-Gly-Gly- Gly(SEQ ID NO:4), Gly-Gly-Ala-Pro-Gly-Asp-Val-Lys-Arg (SEQ ID NO:5), Arg-Arg-Ala-Pro-Gly-Asp-Val-Gly-Gly (SEQ ID NO:6), Gly-Gly-Tyr-Pro-Gly-Asp-Val-Lys-Arg (SEQ ID NO:7), Arg-Arg-Tyr-Pro-Gly-Asp-Val-Gly-Gly (SEQ ID NO:8), Gly-Gly-His-Pro-Gly-Asp-Val-Lys-Arg (SEQ ID NO:9), or Arg-Arg-His-Pro-Gly-Asp-Val-Gly-Gly (SEQ ID NO:10).

In another aspect the present invention is related to single-chain insulin having biological insulin activity and comprising the B- and the A-chain of human insulin or analogues or derivatives thereof connected by a connecting peptide, wherein the connecting peptide has from 5-11 amino acid residues provided that single-chain insulins with a pI above about 6.5 will comprise at least one amino acid residue substitution and/or deletion in the A- and/or B chains compared to the human insulin A- and B-chains or at least one lysine residue in the A-chain, in the B-chain or in the connecting peptide has been chemically modified by acylation.

In another aspect the present invention is related to single-chain insulin having biological insulin activity and comprising the B- and the A-chain of human insulin or analogues or derivatives thereof connected by a connecting peptide, wherein the connecting peptide has from 5-14, 5-11, 6-10, 6-8, 6-7, 7-9 or 7-8 amino acid residues and wherein at least one lysine residue in the A-chain, in the B-chain or in the connecting peptide has been chemically modified by acylation.

In one embodiment the single-chain insulin is acylated in at least one lysine group in the single-chain insulin molecule. In another embodiment the B29Lys is acylated. In a still further embodiment an inserted lysine in the single-chain insulin molecule is acylated or the B1 N-terminal amino acid residue is acylated.

In one aspect the single-chain insulin is acylated with a fatty acid having from 6 to 24 C, 6-20, 6-18 or 6-14 C-atoms.

In a further aspect the present invention is related to a single-chain insulin being soluble at neutral pH and having a pI below about 6.5.

In a still further the single-chain insulin has a pI from about 4.5 to below about 6.5.

In another aspect the present invention is related to a single-chain insulin wherein at least one lysine residue has been modified by acylation.

In another aspect the single-chain insulin with a chemically unmodified A- and B-chain has an affinity to the human insulin receptor of at least 30% of that of human insulin.

In another aspect the single-chain insulin contains up to two basic amino acid residues separated by at least one non basic amino acid residue in the connecting peptide.

In a further aspect of the present invention the single-chain insulin contains at least one additional basic amino acid in the A or B chain compared to the natural human A and B chains. The basic amino acid residue is preferably introduced by substituting one of the natural amino acid residues in the C-terminal end of the B-chain or in the N-terminal end of the A-chain and in one embodiment of the present invention the residue in position B27 is substituted by an Arg.

In a further aspect of the present invention the single-chain insulin will have an amino acid residue in position A21 of the A chain which is different from the natural amino acid residue Asn. Thus Asn in position A21 may be substituted by any other codable amino acid residue except Cys. In one embodiment the amino acid residue in position A21 may be selected from the group consisting of Ala, Gln, Glu, Gly, His, Ile, Leu, Met, Ser, Thr, Trp, Tyr or Val, in particular Gly, Ala, Ser, and Thr. In a further embodiment A21 is Gly.

In one embodiment of the present invention the single-chain insulin will contain at least one basic amino acid residue in the connecting peptide and a Gly in position A21. In a further embodiment of the present invention the single-chain insulin will have two basic amino acid residues in the connecting peptide and a Gly in position A21.

In another embodiment the single-chain insulin has a connecting peptide with 6-10, 6-9, 6-8, or 6-7 or amino acid residues.

In another embodiment the single-chain insulin has a connecting peptide with from 7-10, 7-9 or from 7-8 amino acid residues.

In another embodiment the connecting peptide has a Gly in the connecting peptide in the penultimate position to the first amino acid residue (A1) in the A-chain.

In a further embodiment the connecting peptide comprises a sequence selected from the group consisting of AGRGSGK (SEQ ID NO:15); AGLGSGK (SEQ ID NO:33); AGMGSGK (SEQ ID NO:45); ASWGSGK (SEQ ID NO:48); TGLGSGQ (SEQ ID NO:22); TGLGRGK (SEQ ID NO:23); TGLGSGK (SEQ ID NO:21); HGLYSGK (SEQ ID NO:50); KGLGSGQ (SEQ ID NO:51); VGLMSGK (SEQ ID NO:56); VGLSSGQ (SEQ ID NO:27); VGLYSGK (SEQ ID NO:28) VGLSSGK (SEQ ID NO:30); VGMSSGK (SEQ ID NO:65); VWSSSGK (SEQ ID NO:76) VGSSSGK (SEQ ID NO:16), and VGMSSGK (SEQ ID NO:106)

In another embodiment the single-chain insulin has the formula

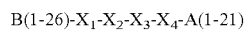

wherein $X_1$ is Thr, Lys or Arg, $X_2$ is Pro, Lys or Asp, $X_3$ is Lys, Pro or Glu, $X_4$ is a peptide sequence of 6-11 amino acid residues, B(1-26) is a peptide chain consisting of the first 26 amino acid residues of the B chain of human insulin counted from the N-terminal end of the B chain or an analogue or derivative thereof, and A(1-21) is the natural insulin A chain or an analogue thereof or derivative thereof, wherein $X_4$ does not contain two adjacent basic amino acid residues and wherein the single-chain insulin has an affinity to the human insulin receptor of at least about 20% of that of human insulin if the single-chain insulin molecule is not chemically modified by acylation.

In another embodiment the single-chain insulin has the formula

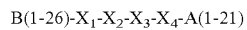

wherein $X_1$ is Thr, Lys or Arg, $X_2$ is Pro, Lys or Asp, $X_3$ is Lys, Pro or Glu, $X_4$ is a peptide sequence of 6-11 amino acid residues, B(1-26) is a peptide chain consisting of the first 26 amino acid residues of the B chain of human insulin counted from the N-terminal end of the B chain or an analogue or derivative thereof, and A(1-21) is the natural insulin A chain or an analogue thereof or derivative thereof, provided that if $X_4$ contains two adjacent basic amino acid residues then at least one of the natural amino acid residues in the B and/or A chain is substituted with another codable amino acid residue or at least one lysine residue in the A-chain, in the B-chain or in the connecting peptide has been chemically modified by acylation or $X_4$ is not one of the following sequences Gly-Gly-Gly-Pro-Gly-Lys-Arg(SEQ ID NO:1), Arg-Arg-Gly-Pro-Gly-Gly-Gly(SEQ ID NO:2), Gly-Gly-Gly-Gly-Gly-Lys-Arg (SEQ ID NO:3), Arg-Arg-Gly-Gly-Gly-Gly-Gly(SEQ ID NO:4), Gly-Gly-Ala-Pro-Gly-Asp-Val-Lys-Arg(SEQ ID NO:5), Arg-Arg-Ala-Pro-Gly-Asp-Val-Gly-Gly(SEQ ID NO:6), Gly-Gly-Tyr-Pro-Gly-Asp-Val-Lys-Arg(SEQ ID NO:7), Arg-Arg-Tyr-Pro-Gly-Asp-Val-Gly-Gly(SEQ ID NO:8), Gly-Gly-His-Pro-Gly-Asp-Val-Lys-Arg(SEQ ID NO:9), or Arg-Arg-His-Pro-Gly-Asp-Val-Gly-Gly(SEQ ID NO:10).

In another embodiment the single-chain insulin has the formula

B(1-26)-$X_1$-$X_2$-$X_3$-$X_4$-A(1-21)

wherein $X_1$ is Thr, Lys or Arg, $X_2$ is Pro, Lys or Asp, $X_3$ is Lys, Pro or Glu, $X_4$ is a peptide sequence of 6-11 amino acid residues, B(1-26) is a peptide chain consisting of the first 26 amino acid residues of the B chain of human insulin counted from the N-terminal end of the B chain or an analogue or derivative thereof, and A(1-21) is the natural insulin A chain or an analogue thereof or derivative thereof, provided that single-chain insulins with a pI above about 6.5 will comprise at least one amino acid residue substitution and/or deletion in the A- and/or B chain compared to the human insulin A- and B-chains or at least one lysine residue in the A-chain, in the B-chain or in the connecting peptide has been chemically modified by acylation.

In another embodiment the single-chain insulin has the formula

B(1-26)-$X_1$-$X_2$-$X_3$-$X_4$-A(1-21)

wherein $X_1$ is Thr, Lys or Arg, $X_2$ is Pro, Lys or Asp, $X_3$ is Lys, Pro or Glu, $X_4$ is a peptide sequence of 5-14, 5-11, 6-10, 6-8, 6-7, 7-9 or 7-8 amino acid residues, B(1-26) is a peptide chain consisting of the first 26 amino acid residues of the B chain of human insulin counted from the N-terminal end of the B chain or an analogue or derivative thereof, and A(1-21) is the natural insulin A chain or an analogue thereof or derivative thereof, wherein at least one lysine residue in the A-chain, in the B-chain or in the connecting peptide has been chemically modified by acylation.

In one aspect $X_1$ is Thr, $X_2$ is Pro, and $X_3$ is Lys.

In another embodiment $X_4$ is a peptide sequence with the following formula $X_a$-$X_b$-$X_c$-$X_d$-$X_e$-$X_f$-$X_g$ (SEQ ID NO: 129) wherein $X_a$ is selected from the group consisting of L, R, T, A, H, Q, G, S and V;

$X_b$ is selected from the group consisting of W, G, S, A, H, R, and T;

$X_c$ is selected from the group consisting of L, Y, M, H, R, T, Q, K, V, S, A, G and P;

$X_d$ is selected from the group consisting of R, A, Y, M, S, N, H, and G;

$X_e$ is selected from the group consisting of S, R, A, T, K P, N M, H, Q, V, and G;

$X_f$ is selected from the group consisting of G and A; and $X_g$ is selected from the group consisting of K, R, P, H, F, T, I, Q, W, and A In a further embodiment $X_a$ is selected from the group consisting of L, R, T, A, H and V;

$X_b$ is selected from the group consisting of W, G, S, A, H, R, and T;

$X_c$ is selected from the group consisting of L, Y, M, H, R, T, Q, K, V, S, A, G and P;

$X_d$ is selected from the group consisting of R, A, Y, M, S, N, H, and G;

$X_e$ is selected from the group consisting of S, R, A, T, K P, and N;

$X_f$ is G; and $X_g$ is selected from the group consisting of K, R, Q and P;

In a further embodiment $X_a$ is selected from the group consisting of T, A V, K;

$X_b$ is G;

$X_c$ is selected from the group consisting of L, Y, M, H, R K, W;

$X_d$ is G;

$X_e$ is selected from the group consisting of S, K;

$X_f$ is G, and $X_g$ is selected from the group consisting of K, R, Q.

In a still further aspect $X_4$ has the sequence $X_5$-G-$X_6$-G-$X_7$-G-$X_8$ (SEQ ID NO:130)

wherein $X_5$ selected from the group consisting of Val, Leu, Arg, Thr, Ala, His, Gln, Gly or Ser, $X_6$ is selected from the group consisting of Leu, Tyr, Met, His, Arg, Thr, Gln, Lys, Val, Ser, Ala, Gly, Pro, $X_7$ is selected from the group consisting of Ser, Arg, Ala, Thr, Lys, Pro, Asn, Met, His, Gln, Val, Gly, and $X_8$ is Lys or Arg.

In a still further aspect $X_5$ selected from the group consisting of Val, Leu, Arg, Thr, Ala, and His, $X_6$ is selected from the group consisting of Leu, Tyr, Met, and His, $X_7$ is selected from the group consisting of Ser, Arg, Ala, Thr, Lys, Pro and Asn and $X_8$ is Lys or Arg.

In one embodiment $X_4$ comprises the sequence SGK. In another embodiment $X_4$ comprises the sequence GSGK (SEQ ID NO:131). In still another embodiment $X_4$ comprises the sequence SSSGK (SEQ ID NO:132).

In one embodiment at least one of the natural amino acid residues in the position B1, B3, B10, B22, B27, B28, B29, A8, A15, A18, and A21 are substituted by another amino acid residue.

In another embodiment the single-chain insulin is a desB1, desB25, desB27, desB28 or desB29 insulin analogue.

In another embodiment $X_4$ comprises the sequence TRXXXGR (SEQ ID NO:112) wherein X is any amino acid.

In a further aspect the present invention is related to single-chain insulin wherein the A- and B-chain are connected with a peptide sequence containing from 6-11 amino acid residues provided that the peptide sequence is not Gly-Gly-Gly-Pro-Gly-Lys-Arg(SEQ ID NO:1), Arg-Arg-Gly-Pro-Gly-Gly-Gly(SEQ ID NO:2), Gly-Gly-Gly-Gly-Gly-Lys-Arg(SEQ ID NO:3), Arg-Arg-Gly-Gly-Gly-Gly-Gly(SEQ ID NO:4), Gly-Gly-Ala-Pro-Gly-Asp-Val-Lys-Arg(SEQ ID NO:5), Arg-Arg-Ala-Pro-Gly-Asp-Val-Gly-Gly(SEQ ID NO:6), Gly-Gly-Tyr-Pro-Gly-Asp-Val-Lys-Arg(SEQ ID NO:7), Arg-Arg-Tyr-Pro-Gly-Asp-Val-Gly-Gly(SEQ ID NO:8), Gly-Gly-His-Pro-Gly-Asp-Val-Lys-Arg(SEQ ID NO:9), or Arg-Arg-His-Pro-Gly-Asp-Val-Gly-Gly(SEQ ID NO:10).

In a further embodiment the connecting peptide is not SANNTK (SEQ ID NO:136), SPNTTK (SEQ ID NO:137), SSNTTK (SEQ ID NO:138) or SRNTTK (SEQ ID NO:139).

The present invention is also related to polynucleotide sequences which code for the claimed single-chain insulins. In a further aspect the present invention is related to vectors containing such polynucleotide sequences and host cells containing such polynucleotide sequences or vectors.

In another aspect, the invention relates to a process for producing the single chain insulins in a host cell, said method comprising (i) culturing a host cell comprising a polynucleotide sequence encoding the single-chain insulins under suitable conditions for expression of said single-chain insulins; and (ii) isolating the single-chain insulins from the culture medium.

In one embodiment of the present invention the host cell is a yeast host cell and in a further embodiment the yeast host cell is selected from the genus *Saccharomyces*. In a further embodiment the yeast host cell is selected from the species *Saccharomyces cerevisiae*.

In a further embodiment the invention is related to a method wherein at lyst one lysine residue in the single-chain insulin molecule is acylated.

In a further embodiment the present invention is related to the use of a single-chain insulin as a pharmaceutical for the treatment of diabetes.

In still a further aspect the present invention is related to pharmaceutical preparations comprising the single-chain insulin of the invention and suitable adjuvants and additives such as one or more agents suitable for stabilization, preservation or isotoni, for example, zinc ions, phenol, cresol, a parabene, sodium chloride, glycerol or mannitol. The zinc content of the present formulations may be between 0 and about 6 zinc atoms per insulin hexamer. The pH of the pharmaceutical preparation may be between about 4 and about 8.5, between about 4 and about 5 or between about 6.5 and about 7.5.

In a still further aspect the present invention is related to pharmaceutical preparations comprising the singe-chain insulin and at least one other pharmaceutical such as rapid acting or protracted insulin analogues, and GLP-1, GLP-2 and exendin and analogues and derivatives thereof. The single-chain insulins according to the present invention may also be used in combination treatment together with rapid acting or protracted insulin analogues, and GLP-1, GLP-2 and exendin and analogues and derivatives thereof or an oral antidiabetic such as a thiazolidindione, metformin and other type 2 diabetic pharmaceutical preparations for oral treatment.

In a further aspect the present invention is related to the use of the single-chain insulin for the preparation of a pharmaceutical preparation for the reducing of blood glucose level in mammalians in particularly for the treatment of diabetes.

In a further embodiment the present invention is related to a method of reducing the blood glucose level in mammalians by administrating a therapeutically active dose of a single-chain insulin according to the invention to a patient in need of such treatment.

DETAILED DESCRIPTION OF THE INVENTION

Figure 1:
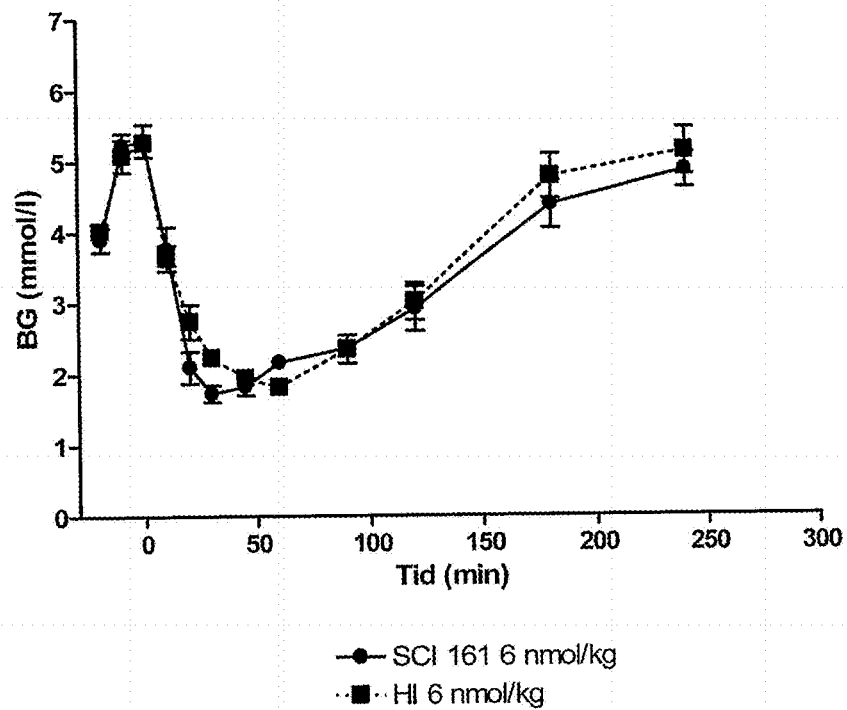
FIG. 1 shows the blood glucose reduction in normal Wistar rats by a single-chain insulin according to the present invention compared to the effect of human insulin. HI is human insulin and SCI is single-chain insulin.
Figure 2:
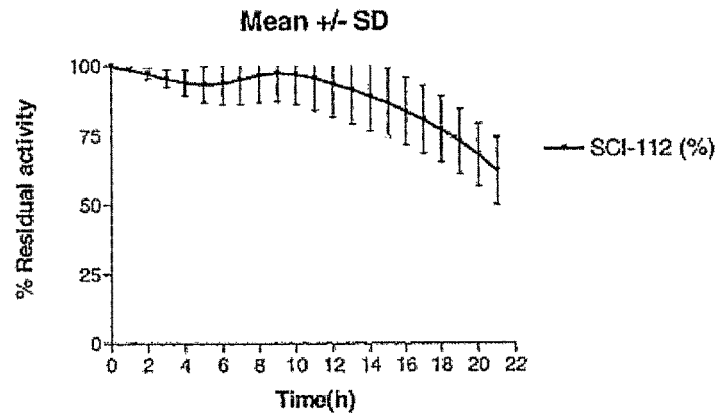
FIG. 2 shows disappearance of a single-chain insulin after s.c. administration in pig
Figure 3:
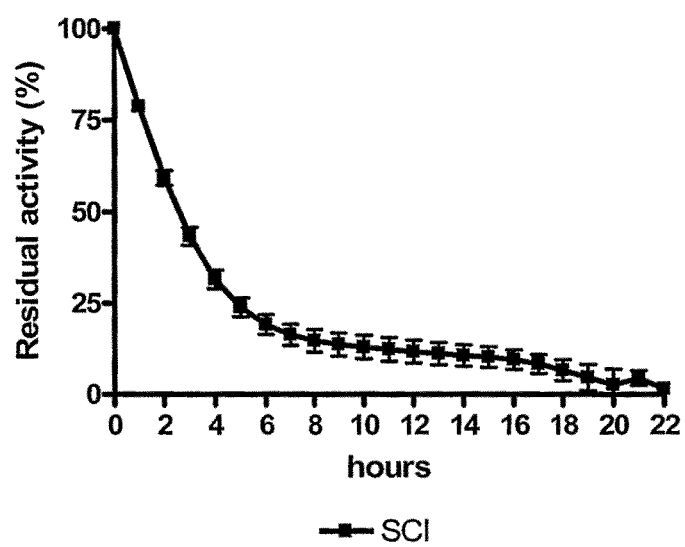
FIG. 3 shows disappearance of another single-chain insulin after s.c. administration in pig.

The single-chain insulins according to the present invention have biological insulin activity. They furthermore have an affinity to the insulin receptor of least 20% of that of human insulin if the single-chain insulin molecule is not chemically modified by acylation. Furthermore, they have an IGF-1 receptor affinity similar to or lower than that of human insulin. The single-chain insulins which are not chemically modified by acylation have an affinity to the insulin receptor of at least 20 percent of that of human insulin. The single-chain insulins according to the present invention are also characterized in having a high physical stability.

Single-chain insulins with at one additional positive charge compared to human insulin and a pI below about 6.5 are soluble at neutral pH and have an action profile like human insulin but have an improved physical stability. If additional positive charge in comparison to human insulin is introduced to the insulin molecule the pI will move upward with one for each added positive charge. By having two additional positive charges compared to human insulin the single-chain insulin will acquire a protracted profile. The single-chain insulin may also be made protracted by introduction of an acyl group in one or more Lys residues or in the N-terminal B1 amino acid residue. The acylated single-chain insulins are soluble at neutral pH and may furthermore be mixable with rapid acting two-chain insulins such as NovoRapid. The single-chain insulins may be selectively acylated in e.q. B29. Alternatively one or more of the natural amino acid residue in the C-terminal end of the B-chain, in the connecting peptide sequence or in the N-terminal end of the A-chain may be substituted with a Lys residue which then in turn can by acylated in a well known manner as disclosed in U.S. Pat. No. 6,500,645

The single-chain insulins of the invention having enhanced stability may also be mixed with soluble long-acting insulins described in U.S. Pat. Nos. 6,500,645 and 5,750,497. The resulting combination retains a biphasic phamacokinetic profile. Furthermore single-chain insulins may feature amino acid substitutions in position B10 and/or B28 decreasing insulin selfassociation.

The connecting peptide in the single-chain insulins of the invention may by up to 14 amino acids long. However a typically length of the connecting peptide will be from 6-10 or 7-10, 7-9 or 7-8.

The connection peptide may in one embodiment have the motives VGSSSGX(SEQ ID NO:122): VGSSSXK (SEQ ID NO:123); VGSSXGK (SEQ ID NO:124): VGSXSGK (SEQ ID NO:125); VGXSSGK (SEQ ID NO:126); VXSSSGK (SEQ ID NO:1127) and XGSSSGK (SEQ ID NO:128) where X is any codable amino acid residue. The following table shows selected meanings of X.

| Connecting peptide | 1. Preference X selected from the group consisting of | 2. Preference X selected from the group consisting of |
| --- | --- | --- |
| VGSSSGX (SEQ ID NO:122) | K and R | P; H; F; T; I; Q; W; and A |
| VGSSSXK (SEQ ID NO:123 | G | A |
| VGSSXGK (SEQ ID NO:124) | S; R; A; T; K; P; and N | M; H; Q; V; and G |
| VGSXSGK (SEQ ID NO:125) | R | A; Y; M; S; N; H and G |
| VGXSSGK (SEQ ID NO:126) | L; Y; M; and H | R; T; Q; K; V; S; A; G; P |
| VXSSSGK (SEQ ID NO:127) | W | G; S; A; H; R; T; P |
| XGSSSGK (SEQ ID NO:128) | L, R, T,A, H, V | Q, G, S |

Another motif for the connecting peptide is TRXXXGR (SEQ ID NO:112) where X can be any codable amino acid residue.

The single-chain insulin may be acylated with an acyl group which may be a linear or branched carboxylic acid having at least 2 carbon atoms and being saturated or unsaturated.

Non-limiting examples of fatty acids are capric acid, lauric acid, tetradecanoic acid (myristic acid), pentadecanoic acid, palmitic acid, heptadecanoic acid, stearic acid, dodecanoic acid, tridecanoic acid, and tetradecanoic acid.

The acyl group may also be a lipophilic substituent selected from the group comprising $CH_3(CH_2)_nCO-$, wherein n is 4 to 24, such as $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.

In one embodiment of the invention the acyl group is a straight-chain or branched alkane $\alpha,\omega$-dicarboxylic acid. In another embodiment of the invention the acyl group has the formula $HOOC(CH_2)_tCO-$ wherein t is an integer of from 2 to 24.

In another embodiment of the invention the acyl group is selected from the group comprising $HOOC(CH_2)_mCO-$, wherein m is 2 to 24, such as $HOOC(CH_2)_{14}CO-$, $HOOC(CH_2)_{16}CO-$, $HOOC(CH_2)_{18}CO-$, $HOOC(CH_2)_{20}CO-$ and $HOOC(CH_2)_{22}CO-$.

The acyl group may be attached to the single-chain insulin by a spacer molecule, e.g. a suitable amino acid residue. The spacer and the acyl group may thus have the formula $CH_3(CH_2)_nCONH-CH(COOH)-(CH_2)_pCO-$, wherein n is an integer of from 4-24, 10-24 or 8-24 and p is an integer of from 1-3. In another embodiment the spacer and the acyl group have the formula $HOOC_3(CH_2)_nCONH-CH(COOH)-(CH_2)_pCO-$, wherein n is an integer of from 4-24 and p is an integer of from 1-3. In another embodiment the combination of the spacer and the acyl group has the formula $CH_3(CH_2)_nCONH-CH(CH_2)_p(COOH)CO-$ wherein n is an integer of from 4-24 and p is an integer of from 1-3 or $HOOC(CH_2)_nCONH-CH((CH_2)_pCOOH)CO-$, wherein n is an integer of from 4-24 and p is an integer of from 1-3.

Finally, the acyl group may by a lithocholic acid as lithocholoyl or choloyl.

If the single-chain insulin is acylated in another position than B29 then the natural lysine residue in B29 is substituted with another amino acid residue e.g. Arg and Ala.

Acylation of the single-chain insulins according to the present invention can be made by a methods analogue to the methods disclosed in U.S. Pat. Nos. 5,750,497 and 5,905,140.

The single-chain insulins are produced by expressing a DNA sequence encoding the single-chain insulin in question in a suitable host cell by well known technique as disclosed in e.g. U.S. Pat. No. 6,500,645. The single-chain insulin is either expressed directly or as a precursor molecule which has an N-terminal extension on the B-chain. This N-terminal extension may have the function of increasing the yield of the directly expressed product and may be of up to 15 amino acid residues long. The N-terminal extension is cleaved in vitro after isolation from the culture broth and will therefore have a cleavage site next to B1. N-terminal extensions of the type suitable in the present invention are disclosed in U.S. Pat. No. 5,395,922, and European Patent No. 765,395A.

The polynucleotide sequence coding for the single-chain insulin of the invention may be prepared synthetically by established standard methods, e.g. the phosphoamidite method described by Beaucage et al. (1981) Tetrahedron Letters 22:1859-1869, or the method described by Matthes et al. (1984) EMBO Journal 3:801-805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequences may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

In a further aspect the invention is related to a vector which is capable of replicating in the selected microorganism or host cell and which carries a polynucleotide sequence encoding the single-chain insulin of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In one embodiment, the recombinant expression vector is capable of replicating in yeast. Examples of sequences which enable the vector to replicate in yeast are the yeast plasmid 2 μm replication genes REP 1-3 and origin of replication.

The vectors of the present invention may contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus*

*amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Mal, TPI, ADH or PGK promoters.

The polynucleotide construct of the invention will also typically be operably connected to a suitable terminator. In yeast a suitable terminator is the TPI terminator (Alber et al. (1982) J. Mol. Appl. Genet. 1:419-434).

The procedures used to ligate the polynucleotide sequence of the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the single-chain insulins of the invention, and subsequently inserting this fragment into a suitable expression vector, or by sequentially inserting DNA fragments containing genetic information for the individual elements (such as the signal, pro-peptide, connecting peptide, A and B chains) followed by ligation.

The present invention also relates to recombinant host cells, comprising a polynucleotide sequence encoding the single-chain insulins of the invention. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In a preferred embodiment, the host cell is a yeast cell. The yeast organism used in the process of the invention may be any suitable yeast organism which, on cultivation, produces large amounts of the single chain insulin of the invention. Examples of suitable yeast organisms are strains selected from the yeast species *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans.*

The transformation of the yeast cells may for instance be effected by protoplast formation followed by transformation in a manner known per se. The medium used to cultivate the cells may be any conventional medium suitable for growing yeast organisms. The secreted insulin precursor of the invention, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

Pharmaceutical Compositions

Compositions containing single-chain insulins of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Usually, the pharmaceutical preparations of this invention are administered subcutaneously. However the single-chain insulins of the invention may also be used in insulin pumps and may be formulated for pulmunal administration.

Single-chain insulins according to the present invention having at least one basic amino acid residues in the peptide sequence connecting B30 or B29 with A1 are expected to have a protracted insulin activity. Due to the additional positive charge the isoelectric point will be increased compared to human insulin and the pH of the pharmaceutical formulation may therefore preferably be below neutral pH e.g. below about 6. When such single-chain insulin preparations are injected they will precipitates at the injection sites where neutral pH exists and will then slowly be dissolved and released from the injection site. The slow release from the injection site will lead to a protracted action which may be wanted for certain applications. Pharmaceutical preparations of the claimed single-chain insulins will contain usual adjuvants and additives and are preferably formulated as an aqueous solution. The aqueous medium is made isotonic, for example, with sodium chloride, sodium acetate or glycerol. Furthermore, the aqueous medium may contain zinc ions, buffers and preservatives. The pH value of the composition is adjusted to the desired value and may be between about 4 to about 8.5, preferably between 7 and 7.5 depending on the isoelectric point, pI, of the single-chain insulin in question.

Consequently, this invention also relates to a pharmaceutical composition containing a single-chain insulin of the invention and optionally one or more agents suitable for stabilization, preservation or isotonicity, for example, zinc ions, phenol, cresol, a parabene, sodium chloride, glycerol or mannitol. The zinc content of the present formulations may be between 0 and about 6 zinc atoms per insulin hexamer. The single-chain insulins may also be formulated with IFD ligands as disclosed in WO 2003027081.

The buffer used in the pharmaceutical preparation according to the present invention may be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

The pharmaceutically acceptable preservative may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19th edition, 1995.

The isotonicity agent may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: The Science and Practice of Pharmacy, 19th edition, 1995.

The single-chain insulins of this invention may also be mixed with other single-chain insulins, human insulin or human insulin analogues or derivatives having a protracted or rapid acting insulin activity to prepare insulin compositions consisting of a mixture of rapid acting and protracted insulin. Examples of such insulin analogues are described e.g. in the European patent applications having the publication Nos. EP 214826, EP 375437 and EP 383472.

The single-chain insulins according to the present invention may also be mixed with other pharmaceutically active compounds such as GLP-1, GLP-2 and exendin or analogues or derivatives thereof. The single-chain insulins according to the present invention may also be used on combination treatment together with an oral antidiabetic such as a thiazolidindione, metformin and other type 2 diabetic pharmaceutical preparation for oral treatment.

Abbreviations and Nomenclature.

By a single-chain insulin is meant a polypeptide sequence of the general structure B-C-A wherein B is the human B insulin chain or an analogue or derivative thereof, A is the human insulin A chain or an analogue or derivative and C is a peptide chain of 5-11 amino acid residues connecting the C-terminal amino acid residue in the B-chain (normally B30) with A1. If the B chain is a desB30 chain the connecting peptide will connect B29 with A1. The single-chain insulin may be derivatized by being acylated at a Lys residue. The single-chain insulin will contain correctly positioned disulphide bridges (three) as in human insulin that is between CysA7 and CysB7 and between CysA20 and CysB19 and an internal disulfide bridge between CysA6 and CysA11.

Analogues of the B and A chains of the human insulin B and A chains are B and A chains having one or more mutations, substitutions, deletions and or additions of the A and/or B amino acid chains relative to that of the human insulin molecule. The insulin analogues are preferably such wherein one or more of the naturally occurring amino acid residues, preferably one, two, or three of them, have been substituted by another codable amino acid residue. In one embodiment, the instant invention comprises analogue molecules having on or more of the position B1, B3, B10, B22; B27, B28, B29, A8, A15 or A22 relative to the natural human insulin molecule as explained in further details below.

DesB30 or B(1-29) refers to a natural insulin B chain or an analogue thereof lacking the B30 amino acid residue. B(1-26) is a peptide chain consisting of the first 26 amino acid residues of the B chain of human insulin counted from the N-terminal end of the B chain or an analogue or derivatives thereof. A(1-21) means the natural insulin A chain or an analogue or derivative thereof and A(1-20) means the first 20 natural amino acid residues of the A chain of human insulin or an analogue or derivative thereof. The amino acid residues are indicated in the three letter amino acid code or the one letter amino code.

With B1, A1 etc. is meant the amino acid residue in position 1 in the B chain of insulin (counted from the N-terminal end) and the amino acid residue in position 1 in the A chain of insulin (counted from the N-terminal end), respectively.

By insulin analogue as used herein is meant a polypeptide having a molecular structure which formally can be derived from the structure of human insulin. Insulin from other animals thus becomes analogues of human insulin. The structure of an analogue can be derived e.g. by deleting and/or substituting at least one amino acid residue occurring in the natural insulin and/or by adding at least one amino acid residue. The added and/or substituted amino acid residues can either be a codable amino acid residues, defined as a mutation, or other naturally occurring amino acid residues, including D-amino acids, or purely synthetic amino acid residues such as N-methyl amino acids, defined as a substitution. The structure can also be derived from a naturally occurring insulin by insertion of/substitution with a non-peptide moiety, e.g. a retroinverso fragment, or incorporation of non-peptide bonds such as an azapeptide bond (CO substituted by NH) or pseudo-peptide bond (e.g. NH substituted with $CH_2$).

Mutation or substitution of Asn residues improves the chemical stability of insulin and the pharmaceutically preparations hereof. Incorporation of D-amino acids and exchange of natural peptide bonds with non-peptide bonds may render resistance towards proteolytic enzymes.

When residues of Asp and Glu occur in the sequence the peptide chain may continue via iso-peptide bonds, i.e. via the β- or γ-linked carboxyl groups of the side-chains, respectively.

Examples of insulin analogues are such wherein Pro in position 28 of the B chain may be mutated with Asp, Lys, or Ile. In another embodiment Lys at position B29 is mutated with Pro. Furthermore B27 Thr may be mutated with Lys, Arg or Glu. Also, Asn at position A21 may be mutated with Ala, Gln, Glu, Gly, His, Ile, Leu, Met, Ser, Thr, Trp, Tyr or Val, in particular with Gly, Ala, Ser, or Thr and preferably with Gly. Furthermore, Asn at position B3 may be mutated with Thr, Lys, Gln, Glu or Asp, and Asn in position A18 may be mutated with Gln. Further examples of insulin analogues are the deletion analogues des(B1 Phe) insulin; insulin analogues wherein the B-chain has an N-terminal extension and insulin analogues wherein the A-chain has a C-terminal extension, e.g. a Lys.

By insulin derivative as used herein is meant a naturally occurring insulin or an insulin analogue which has been chemically modified in vitro, e.g. by introducing a group in a side chain in one or more positions of the insulin, e.g. a nitro group in a tyrosine residue, or iodine in a tyrosine residue, or by conversion of a free carboxylic group to an ester group or to an amide group, or by converting an amino group to an amide by acylation, or by acylating a hydroxy group rendering an ester, or by alkylation of a primary amine rendering a secondary amine. Other derivatives are obtained by oxidation or reduction of the side-chains of the amino acid residues in the insulin.

The single-chain insulins are named according to the following rule: The sequence starts with the B-chain, continues with the C-peptide and ends with the A-chain. The amino acid residues are named after their respective counterparts in human insulin and mutations and acylations are explicitly described whereas unaltered amino acid residues in the A- and B-chains are not mentioned. For example, an insulin having the following mutations as compared to human insulin A21G, B3Q, B29R, desB30 and the C-peptide TGLGKGQ (SEQ ID NO:19) connecting the C-terminal B-chain and the N-terminal A-chain is named B(1-29)-B3Q-B29R-TGLGKGQ(SEQ ID NO:19)-A(1-21)-A18Q-A21G human insulin.

By acyl group is meant the radical derived from an organic acid by removal of the hydroxyl group, i.e. the R—CO— radical, where R can be either hydrogen, an alkyl group or an O-alkyl group.

By acylation is understood the chemical reaction whereby a hydrogen of an amino group or hydroxy group is exchanged with an acyl group.

With preferential or selective acylation is meant an acylation which occurs in a desired position at a higher degree, preferably at least at two or three times higher degree than in a not desired position. In one embodiment of the present invention the acylation should preferably only take place in the ε-amino group in the LysB29 or in an inserted Lys residue in another position or in the N-terminal B1 amino acid residue.

With activated acid is meant a carboxylic acid in which an activated leaving group has been attached to the acyl carbon enabling reaction with an amino group under formation of a amide bond and release of the leaving group. Activated fatty acids may be activated esters of fatty acids, activated amides of fatty acids and anhydrides or chlorides. Activated fatty acids include derivatives thereof such as esters with 1-hydroxybenzotriazole and N-hydroxysuccinimide.

With fatty acid or acyl group is meant a linear or branched carboxylic acid having at least 2 carbon atoms and being saturated or unsaturated. In one embodiment of the present invention the acyl group is a fatty acid having from 6 to 24 C-atoms.

When an insulin is acylated, the point of attachment and the name of the acyl group is given and in the corresponding structure/sequence, the residue and acyl group in question are expanded. For example:

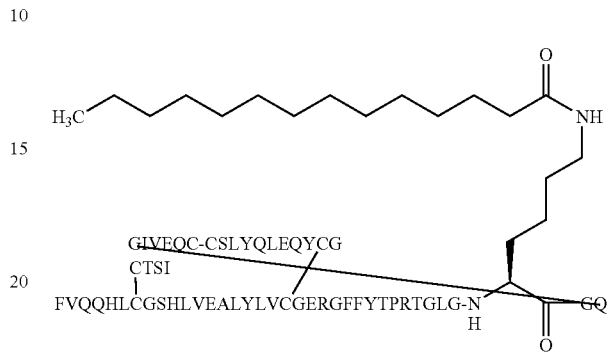

is assigned the name: B(1-29)-B3Q-B29R-TGLGK((eps) myristoyl)GQ-A(1-21)-A18Q-A21G human insulin (SEQ ID NO:133).

By single-chain insulin having insulin activity is meant single-chain insulin with the ability to lower the blood glucose in mammalians as measured in a suitable animal model, which may be a rat, rabbit, or pig model, after suitable administration e.g. by intravenous or subcutaneous administration.

pI is the pH at which a peptide has a zero net charge. The pI of a peptide can be calculated the following formula:

$$\text{Charge}(pH) = \frac{N_{NTerm=H}}{1+10^{pH-8.2}} - \frac{N_{CTerm=OH}}{1+10^{3.2-pH}} - \frac{N_{Asp}}{1+10^{4.0-pH}} - \frac{N_{Glu}}{1+10^{4.5-pH}} + \frac{N_{Lys}}{1+10^{pH-10.4}} + \frac{N_{Arg}}{1+10^{pH-10.4}} - \frac{N_{FreeCys}}{1+10^{9-pH}} - \frac{N_{Tyr}}{1+10^{10-pH}} + \frac{N_{His}}{1+10^{pH-6.4}}$$

$$\text{Charge}(pI) = 0$$

wherein N is the number of occurrence.

By soluble at neutral pH is meant that a 0.6 mM single chain insulin is soluble at neutral pH.

By high physical stability is meant a tendency to fibrillation being less than 50% of that of human insulin. Fibrillation may be described by the lag time before fibril formation is initiated at a given conditions.

By fibrillation is meant a physical process by which partially unfolded insulin molecules interacts with each other to form linear aggregates.

A polypeptide with Insulin receptor and IGF-1 receptor affinity is a polypeptide which is capable of interacting with an insulin receptor and an human IGF-1 receptor in a suitable binding assay. Such receptor assays are well-know within the field and are further described in the examples. The present single-chain insulins will not bind to the IGF-1 receptor or will have a rather low affinity to said receptor. More precisely the present single-chain insulins will have an affinity towards the IGF-1 receptor of substantially the same magnitude or less as that of human insulin when measured as described in the examples.

The affinity of the present single-chain insulins towards the insulin receptor is measured as disclosed in the examples and will typically be between 20 and 200 percent of that of human insulin.

POT" is the *Schizosaccharomyces pombe* triose phosphate isomerase gene, and "TPI1" is the *S. cerevisiae* triose phosphate isomerase gene.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of the invention including yeast aspartic protease 3 (YAP3) signal peptide or any functional analog (Egel-Mitani et al. (1990) YEAST 6:127-137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143-180, Cold Spring Harbor Laboratory, NY and U.S. Pat. No. 4,870,00.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analogue thereof.

In the present context the three-letter or one-letter indications of the amino acids have been used in their conventional meaning as indicated in the following. Unless indicated explicitly, the amino acids mentioned herein are L-amino acids. Further, the left and right ends of an amino acid sequence of a peptide are, respectively, the N- and C-termini unless otherwise specified.

Abbreviations for Amino Acids

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |

-continued

| Amino acid | Tree-letter code | One-letter code |
|---|---|---|
| Aspartic Acid | Asp | D |
| Serine | Ser | S |
| Threonine | Thr | T |

The following abbreviations have been used in the specification and examples:

Bzl=Bn: benzyl
DIEA: N,N-diisopropylethylamine
DMF: N,N-dimethylformamide
tBu: tert-butyl
Glu: Glutamic acid
TSTU: O—(N-succinimidyl)-1,1,3,3-tetramethyluronium tetrafluoroborate
THF: Tetrahydrofuran
EtOAc: Ethyl acetate
DIPEA: Diisopropylethylamine
HOAt: 1-Hydroxy-7-azabenzotriazole
NMP: N-methylpyrrolidin-2-one
TEA: triethyl amine
Su: succinimidyl=2,5-dioxo-pyrrolidin-1-yl
TFA: trifluoracetic acid
DCM: dichloromethane
DMSO: dimethyl sulphoxide
RT: room temperature The present invention is described in further detain in the following examples which are not in any way intended to limit the scope of the invention as claimed. All references cited are herein specifically incorporated by reference for all that is described therein.

EXAMPLES

General Procedures

All expressions plasmids are of the C-POT type, similar to those described in EP 171, 142, which are characterized by containing the *Schizosaccharomyces pombe* triose phosphate isomerase gene (POT) for the purpose of plasmid selection and stabilization in *S. cerevisiae*.

The plasmids also contain the *S. cerevisiae* triose phosphate isomerase promoter and terminator. These sequences are similar to the corresponding sequences in plasmid pKFN1003 (described in WO 90/100075) as are all sequences except the sequence of the EcoRI-XbaI fragment encoding the fusion protein of the leader and the insulin product. In order to express different fusion proteins, the EcoRI-XbaI fragment of pKFN1003 is simply replaced by an EcoRI-XbaI fragment encoding the leader-insulin fusion of interest. Such EcoRI-XbaI fragments may be synthesized using synthetic oligonucleotides and PCR according to standard techniques.

Yeast transformants were prepared by transformation of the host strain *S. cerevisiae* strain MT663 (MATa/MATα pep4-3/pep4-3 HIS4/his4 tpi::LEU2/tpi::LEU2 Cir$^+$). The yeast strain MT663 was deposited in the Deutsche Sammlung von Mikroorganismen und Zellkulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na₂EDTA, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM CaCl₂, 10 mM Tris HCl (Tris=Tris(hydroxymethyl)aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM CaCl₂, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl₂) and incubated at 30° C. for 2 hours. The suspension was then centrifuged and the pellet resuspended in 0.5 ml of 1.2 M sorbitol. Then, 6 ml of top agar (the SC medium of Sherman et al. (1982) *Methods in Yeast Genetics*, Cold Spring Harbor Laboratory) containing 1.2 M sorbitol plus 2.5% agar) at 52° C. was added and the suspension poured on top of plates containing the same agar-solidified, sorbitol containing medium.

*S. cerevisiae* strain MT663 transformed with expression plasmids was grown in YPD for 72 h at 30° C.

Example 1

A number of single-chain insulins were produced as described above and isolated from the culture medium and purified for further testing. The single-chain insulins were tested for biological insulin activity as measured by binding affinity to the human insulin receptor relative to that of human insulin as described below.

Furthermore, the affinity to the IGF-1 was tested as described below. The results are shown in Table 1 where "IR" means human insulin receptor binding relative to that of human insulin.

TABLE 1

| Single-chain Insulin (PAK) | Connecting peptide | Amino acid substitutions | IR | Human IGF-1 receptor binding relative to human insulin |
|---|---|---|---|---|
| 1606 | RSFDGK (SEQ ID NO:34) | | 41% | |
| 1663 | TVGSSRGK (SEQ ID NO:35) | | 46% | |
| 1664 | TGSSRGK (SEQ ID NO:36) | | 43% | |
| 1735 | VGRSSGK (SEQ ID NO:31) | [A21G] | 143% | |
| 1754 | AGRGSGP (SEQ ID NO:18) | | 53% | |
| 1767 | AGRGSGP (SEQ ID NO:18) | [A18Q_A21G] | 28% | |
| 1801 | AGRGSGK (SEQ ID NO:15) | | 129% | |
| 1817 | AGRGSGK (SEQ ID NO:15) | [A21G] | 63% | |
| 1800 | AGRGSGK (SEQ ID NO:15) | [A18Q_A21G] | 175% | |
| 1805 | AGRGSGK (SEQ ID NO:15) | [B3Q_A18Q_A21G] | 83% | |
| 1808 | AGRGSGK (SEQ ID NO:15) | [B1G_B3Q_A18Q_A21G] | 86% | |
| 1802 | AGRGK (SEQ ID NO:32) | [A18Q_A21G] | 25% | |
| 1786001 | AGLGDGK (SEQ ID NO:37) | | 50% | |
| 1786017 | AGLGVGK (SEQ ID NO:38) | | 47% | |
| 1786026 | AGLGMGK (SEQ ID NO:39) | | 35% | |
| 1786030 | AGLGSGK (SEQ ID NO:33) | | 197% | |
| 1786036 | AGLGYGK (SEQ ID NO:40) | | 35% | |

TABLE 1-continued

| Single-chain Insulin (PAK) | Connecting peptide | Amino acid substitutions | Human IGF-1 receptor binding relative to IR human insulin |
|---|---|---|---|
| 1786044 | AGLGQGK (SEQ ID NO:41) | | 22% |
| 1786046 | AGLGGGK (SEQ ID NO:42) | | 68% |
| 1786053 | AGLGRGK (SEQ ID NO:43) | | 54% |
| 1764 | AGLGSGK (SEQ ID NO:33) | [A18Q_A21G] | 120% |
| 1816 | AGLGSGQ (SEQ ID NO:44) | [B3Q_A18Q] | 37% |
| 1757 | AGLGSGK (SEQ ID NO:24) | | 116% |
| 1755 | AGMGSGK (SEQ ID NO:45) | | 137% |
| 1762 | AGMGSGP (SEQ ID NO:25) | [A18Q_A21G] | 20% |
| 1672 | AGSSSGK (SEQ ID NO:46) | | 31% |
| 1784 | WASGSGK (SEQ ID NO:47) | [A18Q_A21G] | 23% |
| 1785 | ASWGSGK (SEQ ID NO:48) | [A18Q_A21G] | 136% |
| 1796 | AWSGSGK (SEQ ID NO:49) | [A18Q_A21G] | 102% |
| 1781 | TGLGSGQ (SEQ ID NO:22) | | 122% |
| 1782 | TGLGSGK (SEQ ID NO:21) | | 130% |
| 1783 | TGLGRGK (SEQ ID NO:23) | | 86% |
| 1810 | TGLGSGQ (SEQ ID NO:22) | [A18Q_A21G] | 73% |
| 1811 | TGLGSGK (SEQ ID NO:21) | [A18Q_A21G] | 136% |
| 1812 | TGLGRGK (SEQ ID NO:23) | [A18Q_A21G] | 118% |
| 1820 | TGLGKGQ (SEQ ID NO:19) | [B3Q_B29R_A18Q_A21G] | 55% |
| 1821 | TGLGSGK (SEQ ID NO:21) | [B3Q_B29R_A18Q_A21G] | 128% |
| 1835 | TGLGKGQ (SEQ ID NO:19) | [B29E_A18Q] | 50% |
| 1837 | TGLGKGQ (SEQ ID NO:19) | [B29A_A18Q] | 71% |
| 1838 | TGLGKGQ (SEQ ID NO:19) | [B29R_A18Q] | 113% |
| 1845 | TGLGKGQ (SEQ ID NO:19) | [B27E_B29A_A18Q] | 20% |
| 1846 | TGLGKGR (SEQ ID NO:20) | [B29A_A18Q] | 92% |

TABLE 1-continued

| Single-chain Insulin (PAK) | Connecting peptide | Amino acid substitutions | Human IGF-1 receptor binding relative to IR human insulin |
|---|---|---|---|
| 1847 | TGLGKGR (SEQ ID NO:20) | [B27E_B29A_A18Q] | 82% |
| 1848 | TGLGKGR (SEQ ID NO:20) | [B27E_B29E_A18Q] | 40% |
| 1849 | TGLGKGR (SEQ ID NO:20) | [B29E_A18Q] | 60% |
| 1850 | TGLGSGQ (SEQ ID NO:22) | [B10R] | 31% |
| 1864 | TGLGSGK (SEQ ID NO:21) | [B3K_A18Q_A21G] | 301% |
| 1877 | TGLGSGK (SEQ ID NO:21) | [B28D_A18Q] | 140% |
| 1881 | TGLGSGK (SEQ ID NO:21) | [A18K_A21G] | |
| 1891 | TGLGSGQ (SEQ ID NO:22) | [B10A_A18Q] | 34% |
| 1892 | TGLGSGQ (SEQ ID NO:22) | [desB1_B3Q_B10A_A18Q] | 38% |
| 1893 | TGLGSGQ (SEQ ID NO:22) | [B10Q_A18Q] | 51% |
| 1894 | TGLGSGQ (SEQ ID NO:22) | [desB1_B3Q_B10Q_A18Q] | 38% |
| 1791 | HGLYSGK (SEQ ID NO:50) | [A18Q_A21G] | 226% |
| 1818 | KGLGSGQ (SEQ ID NO:51) | [B3Q_B29R_A18Q_A21G] | 125% |
| 1819 | C (SEQ ID NO:26) | [B3Q_B29R_A18Q_A21G] | 47% |
| 1824 | GRGSGK (SEQ ID NO:52) | [B1G_B3Q_A18Q_A21G] | 75% |
| 1727 | VGLSSGD (SEQ ID NO:53) | | 54% |
| 1728 | VGLSSGQ (SEQ ID NO:54) | | 151% |
| 1730 | VGLRSGK (SEQ ID NO:55) | | 306% |
| 1731 | VGLMSGK (SEQ ID NO:56) | | 247% |
| 1841 | VGLGGGPGAGK (SEQ ID NO:29) | | 43% |
| 1842 | VGLGPGAGK (SEQ ID NO:58) | | 41% |
| 1813 | VGLGGGPGAGK (SEQ ID NO:59) | [A18Q] | 39% |
| 1814 | VGLGGPGAGK (SEQ ID NO:60) | [A18Q] | 43% |
| 1815 | VGLGPGAGK (SEQ ID NO:58) | [A18Q] | 57% |
| 1787 | VGLSSGQ (SEQ ID NO:27) | [A18Q_A21G] | 123% |

TABLE 1-continued

| Single-chain Insulin (PAK) | Connecting peptide | Amino acid substitutions | IR | Human IGF-1 receptor binding relative to human insulin |
|---|---|---|---|---|
| 1788 | VGLYSGK (SEQ ID NO:28) | [A18Q_A21G] | 323% | |
| 1789 | VGLRSGK (SEQ ID NO:55) | [A18Q_A21G] | 248% | |
| 1790 | VGLMSGK (SEQ ID NO:56) | [A18Q_A21G] | 261% | |
| 1734 | VGLSSGK (SEQ ID NO:30) | [A21G] | 211% | |
| 1866 | VGLSSGQ (SEQ ID NO:27) | [A18Q] | 196% | |
| 1869 | VGLSSGQ (SEQ ID NO:27) | [B22K_B29A_A18Q] | 69% | |
| 1870 | VGLSSGQ (SEQ ID NO:27) | [B29A_A15K_A18Q] | | |
| 1871 | VGLSSGQ (SEQ ID NO:27) | [B29A_A18K] | 82% | |
| 1872 | VGLSSGQ (SEQ ID NO:27) | [B3K_B29A_A18Q] | | |
| 1854 | VGLYSGK (SEQ ID NO:28) | [B29E_A18Q] | 40% | |
| 1875 | VGLSSGQ (SEQ ID NO:27) | [B28K_B29A_A18Q] | 35% | |
| 1876 | VGLSSGQ (SEQ ID NO:27) | [B27K_B29A_A18Q] | 38% | |
| 1878 | VGLSSGQ (SEQ ID NO:27) | [B3K_A18K_A21G] | 172% | |
| 1879 | VGLSSGQ (SEQ ID NO:27) | [B29A_A18Q] | 92% | |
| 1880 | VGLSSGQ (SEQ ID NO:27) | [B1G_B3Q_A18Q_A21G] | 54% | |
| 1855 | VGLYSGK (SEQ ID NO:28) | [B28D_A18Q] | 221% | |
| 1858 | VGLGGGPGKGR (SEQ ID NO:121) | [B29E_A18Q] | 36% | |
| 1861 | VGLGKGPGAGK (SEQ ID NO:61) | [A18Q_A21G] | 36% | |
| 1862 | VGLGGGPGAGK (SEQ ID NO:29) | [B3K_A18Q_A21G] | 42% | |
| 1884 | VGLSSGQ (SEQ ID NO:27) | [B29A_A8K_A18Q] | 89% | |
| 1896 | VGLSSGQ (SEQ ID NO:27) | [B29A_A18Q_A22K] | 38% | |
| 1863 | HGRGSGK (SEQ ID NO:62) | [A18Q_A21G] | 122% | |
| 1873 | KGLSSGQ (SEQ ID NO:63) | [B29A_A18Q] | 60% | |
| 1874 | VKLSSGQ (SEQ ID NO:64) | [B29A_A18Q] | 83% | |
| 1688023 | VGRSSGK (SEQ ID NO:31) | | 97% | |

TABLE 1-continued

| Single-chain Insulin (PAK) | Connecting peptide | Amino acid substitutions | Human IGF-1 receptor binding relative to IR human insulin |
|---|---|---|---|
| 1688059 | VGMSSGK (SEQ ID NO:65) | | 112% |
| 1655 | TGSSSGK (SEQ ID NO:66) | | 43% |
| 1656 | TVGSSSGK (SEQ ID NO:67) | | 57% |
| 1689007 | LGSSSGK (SEQ ID NO:68) | | 49% |
| 1689008 | RGSSSGK (SEQ ID NO:69) | | 54% |
| 1689012 | QGSSSGK (SEQ ID NO:70) | | 34% |
| 1689021 | GGSSSGK (SEQ ID NO:71) | | 23% |
| 1689037 | SGSSSGK (SEQ ID NO:72) | | 49% |
| 1724005 | VDSSSGK (SEQ ID NO:73) | | 32% |
| 1724012 | VPSSSGK (SEQ ID NO:74) | | 80% |
| 1724014 | VESSSGK (SEQ ID NO:75) | | 40% |
| 1724015 | VWSSSGK (SEQ ID NO:76) | | 298% |
| 1724016 | VTSSSGK (SEQ ID NO:77) | | 51% |
| 1724029 | VASSSGK (SEQ ID NO:78) | | 81% |
| 1724040 | VSSSSGK (SEQ ID NO:79) | | 73% |
| 1724042 | VRSSSGK (SEQ ID NO:80) | | 76% |
| 1769013 | QVGSSSGK (SEQ ID NO:81) | [A18Q_A21G] | 33% |
| 1769015 | EVGSSSGK (SEQ ID NO:82) | [A18Q_A21G] | 42% |
| 1769020 | SVGSSSGK (SEQ ID NO:83) | [A18Q_A21G] | 51% |
| 1769027 | LVGSSSGK (SEQ ID NO:84) | [A18Q_A21G] | 68% |
| 1769033 | PVGSSSGK (SEQ ID NO:85) | [A18Q_A21G] | 37% |
| 1769040 | VVGSSSGK (SEQ ID NO:86) | [A18Q_A21G] | 29% |
| 1769053 | GVGSSSGK (SEQ ID NO:87) | [A18Q_A21G] | 37% |
| 1769062 | PVGSSSGK (SEQ ID NO:85) | [A18Q_A21G] | 56% |
| 1711 | RGSSSGK (SEQ ID NO:120) | | 65% |

TABLE 1-continued

| Single-chain Insulin (PAK) | Connecting peptide | Amino acid substitutions | IR | Human IGF-1 receptor binding relative to human insulin |
|---|---|---|---|---|
| 1674 | VGASSGK (SEQ ID NO:86) | | 49% | |
| | VGSSNGK (SEQ ID NO:87) | | 48% | |
| 1638077 | VGSSRGK (SEQ ID NO:17) | | 61% | 0.1% |
| | VGSSGK (SEQ ID NO:88) | | | |
| 1676 | VGSSAGK (SEQ ID NO:119) | | 22% | |
| 1723 | VGSSRGK (SEQ ID NO:17) | [A21G] | 33% | |
| 1617 | VGSSNGK (SEQ ID NO:118) | | 48% | |
| 1677 | VGSSSAK (SEQ ID NO:89) | | 22% | |
| 1766 | VGSSSGK (SEQ ID NO:16) | | 62% | 0.05% |
| 1724004 | VGSSSGK (SEQ ID NO:16) | | 72% | |
| 1760016 | VGSSSGK (SEQ ID NO:16) | [B10D] | 135% | |
| 1760023 | VGSSSGK (SEQ ID NO:16) | [B10E] | 77% | |
| 1760043 | VGSSSGK (SEQ ID NO:16) | [B10Q] | 67% | |
| 1760056 | VGSSSGK (SEQ ID NO:16) | [B10E] | 83% | |
| 1760059 | VGSSSGK (SEQ ID NO:16) | [B10N] | 48% | |
| 1738 | VGSSSGK (SEQ ID NO:16) | [A18Q] | 89% | |
| 1740 | VGSSSGK (SEQ ID NO:16) | [B1G_B3Q_A18Q_A21G] | 90% | |
| 1741 | VGSSSGK (SEQ ID NO:16) | [B1G] | 112% | |
| 1744 | VGSSSGK (SEQ ID NO:16) | [A18Q_A21G] | 80% | |
| 1860 | VGSSSGK (SEQ ID NO:16) | [B3K_A18Q_A21G] | 83% | |
| 1733 | VGSSSGK (SEQ ID NO:16) | [A21G] | 42% | |
| 1712 | VGSSSGK (SEQ ID NO:16) | B27R | 85% | |
| 1719 | VGHSRGK (SEQ ID NO:90) | | 103% | |
| 1721 | HGSSRGK (SEQ ID NO:91) | | 118% | |
| | VGSASGK (SEQ ID NO:92) | | 80% | |

TABLE 1-continued

| Single-chain Insulin (PAK) | Connecting peptide | Amino acid substitutions | IR | Human IGF-1 receptor binding relative to human insulin |
|---|---|---|---|---|
| 1687009 | VGSNSGK (SEQ ID NO:93) | | 48% | |
| 1708 | VGSRSGK (SEQ ID NO:94) | | 128% | 0.2% |
| 1718 | VGSHRGK (SEQ ID NO:95) | | 69% | |
| 1687030 | VGSGSGK (SEQ ID NO:96) | | 55% | |
| 1687033 | VGSYSGK (SEQ ID NO:97) | | 80% | 0.2% |
| 1687046 | VGSMSGK (SEQ ID NO:98) | | 82% | 0.1% |
| 1688001 | VGPSSGK (SEQ ID NO:99) | | 48% | |
| 1688005 | VGTSSGK (SEQ ID NO:100) | | 75% | |
| 1688006 | VGQSSGK (SEQ ID NO:101) | | 56% | |
| 1688007 | VGYSSGK (SEQ ID NO:102) | | 95% | 0.2% |
| 1688011 | VGLSSGK (SEQ ID NO:30) | | 132% | 0.1% |
| 1688012 | VGKSSGK (SEQ ID NO:103) | | 93% | |
| 1688014 | VGGSSGK (SEQ ID NO:104) | | 51% | |
| 1709 | VGRSSGK (SEQ ID NO:105) | | 97% | 0.5% |
| 1688028 | VGMSSGK (SEQ ID NO:106) | | 127% | 0.2% |
| 1688056 | VGVSSGK (SEQ ID NO:107) | | 59% | |
| | VGHSSGK (SEQ ID NO:108) | | 112% | 0.15% |
| | LGSSGK (SEQ ID NO:113) | | 49% | |
| | RGSSGK (SEQ ID NO:114) | | 54% | 0.5% |
| | QGSSGK (SEQ ID NO:115) | | 34% | |
| | GGSSGK (SEQ ID NO:116) | | 23% | |
| | SGSSGK (SEQ ID NO:117) | | 49% | |
| | GSSGK (SEQ ID NO:109) | | 35% | |
| | QGSSGK (SEQ ID NO:110) | | 36% | |

TABLE 1-continued

| Single-chain Insulin (PAK) | Connecting peptide | Amino acid substitutions | Human IGF-1 receptor binding relative to IR human insulin |
|---|---|---|---|
| | TRSSSGR (SEQ ID NO:111) | | |

Insulin receptor binding of single-chain insulins with the motive of the connecting peptide of TRXXXGR (SEQ ID NO:112) in percent of that of human insulin

| B chain | XXX | A-chain | Insulin receptor Binding IR | Human IGF-1 receptor binding |
|---|---|---|---|---|
| B(1-29) | YGS | A(1-21) | | |
| B((1-29) | SSN | A(1-21) | 61% | 0.1% |
| B(1-29) | LSQ | A(1-21) | 62% | 0.05% |
| B(1-29) | PKS | A(1-21) | 18% | |
| B(1-29) | LGG | A(1-21) | 43% | |
| B(1-29) | VTG | A(1-21) | 57% | |
| B(1-29) | STN | A(1-21) | 46% | |
| B(1-29) | LES | A(1-21) | 43% | |
| B(1-29) | IDS | A(1-21) | 31% | |
| B(1-29) | NSQ | A(1-21) | 38% | |
| B(1-29) | PSY | A(1-21) | 49% | |
| B(1-29) | ENT | A(1-21) | 34% | |
| B(1-29) | TPQ | A(1-21) | 22% | |
| B(1-29) | NRT | A(1-21) | 22% | |

Example 2

B(1-29)-B3Q-B29R-TGLGK((eps)myristoyl)GQ-A(1-21)-A18Q-A21G Human insulin (SEQ ID NO: 133) (PAK1820)

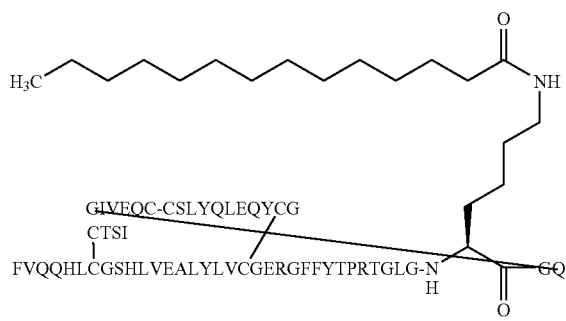

B(1-29)-B3Q-B29R-TGLGKGQ-A(1-21)-A18Q-A21G human insulin(SEQ ID NO:133) (150 mg, 24 μmol) was dissolved in aqueous sodium carbonate (100 mM, 2.8 mL) and added a solution of myristic acid N-hydroxysuccinimide ester (7.7 mg, 24 μmol, may be prepared according to B. Faroux-Corlay et al., J. Med. Chem. 2001, 44, 2188-2203) in N-methylpyrrolidin-2-one (0.5 mL). The resulting mixture was added more N-methylpyrrolidin-2-one (3 mL) and aqueous sodium carbonate (100 mM, 0.8 mL), to pH 10-11. The resulting mixture was stirred at room temperature for 50 minutes. pH was adjusted to 5.5 with 1N hydrochloric acid. The solid formed was isolated by centrifugation and decantation. The residue was purified by preparative HPLC in two runs on a Jones Kromasil RP18 5 μm, 15×225 mm column, using a flow of 8 mL/min with the following gradient:

| 0.00-5.00 min: | 10% CH3CN + 0.1% TFA, |
|---|---|
| 5.00-35.0 min: | 10%-50% CH₃CN + 0.1% TFA, |
| 35.0-45.0 min: | 50%-90% CH₃CN + 0.1% TFA. |

Pure fractions were pooled and lyophilised to afford 12 mg of the title compound.
Nanoflow Electrospray MS: m/z=6541 (M+1).
HPLC: Rt=15.44 min.
Column: C4, 5μ, 150×4 60 mm "phenomenex, Jupiter".
Injection 20 μl.
Flow: 1.5 ml/min
Solvents:
A: 80% 0.0125 M Tris, 0.0187 M (NH4)2SO4 pH=7, 20% CH3CN.
B: 80% CH₃CN, 20% water.
Gradient:

| 0.00-20.00 min: | 5%-55% B, |
|---|---|
| 20.0-22.0 min: | 55%-80% B, |
| 22.0-24.0 min: | 80% B, |
| 24.0-25.0 min: | 80%-5% B, |
| 25.0-32.0 min: | 5% B. |

Example 3

B(1-29)-B3Q-B29R-TGLGK((eps)octadecandioyl)GQ-A(1-21)-A18Q-A21G Human insulin (SEQ ID NO:133) (PAK1820)

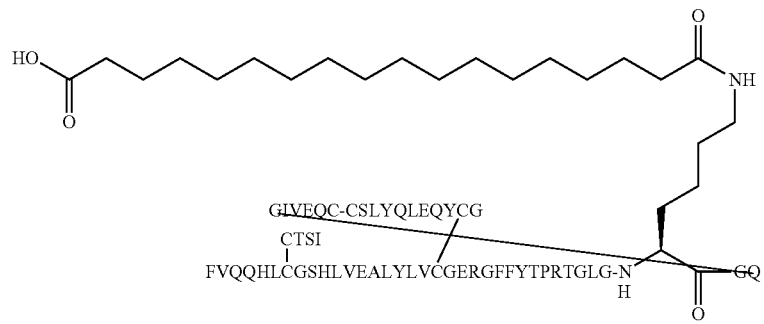

B(1-29)-B3Q-B29R-TGLGKGQ-A(1-21)-A18Q-A21G human insulin (SEQ ID NO:133) (150 mg, 24 µmol) was dissolved in aqueous sodium carbonate (100 mM, 2.8 mL) and added a solution of succinimidyl tert-butyl octadecandioate (prepared in analogy with the method described in example 4 (11 mg, 24 µmol) in acetonitrile (2 mL). The resulting mixture was added more acetonitrile (2 mL). pH of the mixture was 10-11. The resulting mixture was stirred at room temperature for 1 hour. pH was adjusted to 5.86 with 1N hydrochloric acid. The solid formed was isolated by centrifugation and decantation. The residue was purified by preparative HPLC in two runs on a Jones Kromasil RP18 5 µm, 15×225 mm column, using a flow of 8 mL/min with the following gradient:

| | |
|---|---|
| 0.00-5.00 min: | 10% CH$_3$CN, |
| 5.00-35.0 min: | 10%-50% CH$_3$CN, |
| 35.0-45.0 min: | 50%-90% CH$_3$CN. |

Pure fractions were pooled and lyophilised to afford 48 mg of intermediary B(1-29)-B3Q-B29R-TGLGK((eps)tert-butyl octadecandioyl)GQ-A(1-21)-A18Q-A21G human insulin (SEQ ID NO:133).

The above B(1-29)-B3Q-B29R-TGLGK((eps)tert-butyl octadecandioyl)GQ-A(1-21)-A18Q-A21G human insulin (SEQ ID NO:133) (48 mg) was added trifluoroacetic acid (1.8 ml) and the mixture was gently stirred at room temperature for 35 minutes. The mixture was concentrated in vacuo and stripped with dichloromethane twice. The residue was purified by preparative HPLC in two runs on a Macherey-Nagel SP 250/21 Nucleosil 300-7 C4 column, using a flow of 8 mL/min with the following gradient:

| | |
|---|---|
| 0.00-5.00 min: | 10% CH$_3$CN, |
| 5.00-30.0 min: | 10%-50% CH$_3$CN, |
| 30.0-35.0 min: | 50%-90% CH$_3$CN. |
| 35.0-40.0 min: | 100% CH$_3$CN. |

This afforded 19 mg B(1-29)-B3Q-B29R-TGLGK((eps) octadecandioyl)GQ-A(1-21)-A18Q-A21G human insulin (SEQ ID NO:133)

Nanoflow Electrospray MS: m/z=6626 (calculated: 6626)
HPLC: Rt=12.62 min.
Column: C4, 5µ, 150×4 60 mm "phenomenex, Jupiter".
Flow: 1.5 ml/min
Solvents:
A: 80% 0.0125 M Tris, 0.0187 M (NH$_4$)$_2$SO$_4$ pH=7, 20% CH$_3$CN.
B: 80% CH$_3$CN, 20% water.
Gradient:

| | |
|---|---|
| 0.00-20.00 min: | 5%-55% B, |
| 20.0-22.0 min: | 55%-80% B, |
| 22.0-24.0 min: | 80% B, |
| 24.0-25.0 min: | 80%-5% B, |
| 25.0-32.0 min: | 5% B. |

Example 4

B(1-29)-B3Q-B29R-TGLGK((eps)hexadecandioyl-γ-L-Glu)GQ-A(1-21)-A 8Q-A21 G Human insulin (SEQ ID NO:133)(PAK1820)

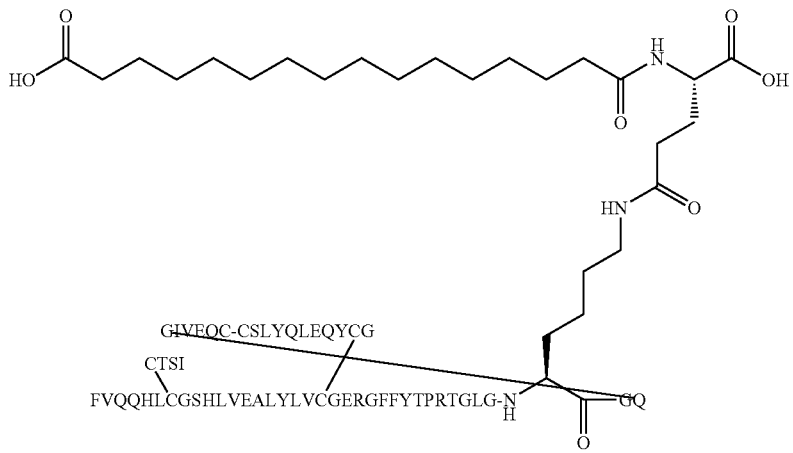

This compound was prepared similarly as described in example 2 from acylation of B(1-29)-B3Q-B29R-TGLGKGQ-A(1-21)-A18Q-A21G human insulin (SEQ ID NO:133) with tert-butyl hexadecandioyl-γ-L-Glu(OSu)-OtBu, followed by TFA mediated deprotection of the tBu esters.

Data for the title compound:
MALDI-TOF: m/z=6727 (calculated: 6727)
HPLC: Rt=10.15 min.
Column: C4, 5µ, 150×4 60 mm "phenomenex, Jupiter".
Flow: 1.5 ml/min
Solvents:
A: 80% 0.0125 M Tris, 0.0187 M (NH$_4$)$_2$SO$_4$ pH=7, 20% CH$_3$CN.
B: 80% CH$_3$CN, 20% water.
Gradient:

| | |
|---|---|
| 0.00-20.00 min: | 5%-55% B, |
| 20.0-22.0 min: | 55%-80% B, |
| 22.0-24.0 min: | 80% B, |
| 24.0-25.0 min: | 80%-5% B, |
| 25.0-32.0 min: | 5% B. |

Preparation of Tert-Butyl Hexadecandioyl-γ-L-Glu(OSu)-OtBu

Hexadecadioic acid (40.0 g, 140 mmol) was suspended in toluene (250 ml) and the mixture was heated to reflux. N,N-dimethylformamide di-tert-butyl acetal (76.3 g, 375 mmol) was added drop-wise over 4 hours. The mixture was refluxed overnight. The solvent was removed in vacuo at 50° C., and the crude material was suspended in DCM/AcOEt (500 ml, 1:1) and stirred for 15 mins. The solids were collected by filtration and triturated with DCM (200 ml). The filtrated were evaporated in vacuo to give crude mono-tert-butyl hexadecandioate, 30 grams. This material was suspended in DCM (50 ml), cooled with ice for 10 mins, and filtered. The solvent was removed in vacuo to leave 25 gram crude mono-tert-butyl hexadecandioate, which was recrystallized from heptane (200 ml) to give mono-tert-butyl hexadecandioate, 15.9 g (33%). Alternatively to recrystallization, the mono-ester can be purified by silica gel chromatography eluting with AcOEt/heptane.

1H-NMR (CDCl$_3$) δ: 2.35 (t, 2H), 2.20 (t, 2H), 1.65-1.55 (m, 4H), 1.44 (s, 9H), 1.34-1.20 (m, 20H).

The mono tert-butyl ester (2 g, 5.8 mmol) was dissolved in THF (20 ml) and treated with TSTU (2.1 g, 7.0 mmol) and DIEA (1.2 ml, 7.0 mmol) and stirred overnight. The mixture was filtered, and the filtrate was evaporated in vacuo. The residue was dissolved in AcOEt and washed twice with cold 0.1 M HCl and water. Drying over MgSO$_4$ and evaporation in vacuo gave succinimidyl tert-butyl hexadecandioate, 2.02 g (79%).

1H-NMR (CDCl$_3$) δ: 2.84 (s, 4H), 2.60 (t, 2H), 2.20 (t, 2H), 1.74 (p, 2H), 1.56 (m, 2H), 1.44 (s, 9H), 1.40 (m, 2H), 1.30-1.20 (m, 18H).

Succinimidyl tert-butyl hexadecandioate (1 g, 2.27 mmol) was dissolved DMF (15 ml) and treated with L-Glu-OtBu (0.51 g, 2.5 mmol) and DIEA (0.58 ml, 3.41 mmol) and the mixture was stirred overnight. The solvent was evaporated in vacuo, and the crude product was dissolved in AcOEt, and washed twice with 0.2M HCl, with water and brine. Drying over MgSO4 and evaporation in vacuo gave tert-butyl hexadecandioyl-γ-L-Glu-OtBu, 1.2 g (100%).

1H-NMR (CDCl$_3$) δ: 6.25 (d, 1H), 4.53 (m, 1H), 2.42 (m, 2H), 2.21 (m, 4H), 1.92 (m, 1H), 1.58 (m, 4H), 1.47 (s, 9H), 1.43 (s, 9H), 1.43-1.22 (m, 18H).

Tert-butyl hexadecandioyl-γ-L-Glu-OtBu (1.2 g, 2.27 mmol) was dissolved in THF (15 ml) and treated with TSTU (0.82 g, 2.72 mmol) and DIEA (0.47 ml, 2.72 mmol) and stirred overnight. The mixture was filtered, and the filtrate was evaporated in vacuo. The residue was dissolved in AcOEt and washed twice with cold 0.1 M HCl and water. Drying over MgSO4 and evaporation in vacuo gave tert-butyl hexadecandioyl-γ-L-Glu(OSu)-OtBu, 1.30 g (92%).

1H-NMR (CDCl$_3$) δ: 6.17 (d, 1H), 4.60 (m, 1H), 2.84 (s, 4H), 2.72 (m, 1H), 2.64 (m, 1H), 2.32 (m, 1H), 2.20 (m, 4H), 2.08 (m, 1H), 1.6 (m, 4H), 1.47 (s, 9H), 1.43 (s, 9H), 1.33-1.21 (m, 20 H).

Example 5

B(1-29)-B27E-B29A-TGLGK((eps)myristoyl)GQ-A(1-21)-A18Q Human insulin (SEQ ID NO:134) (PAK1845)

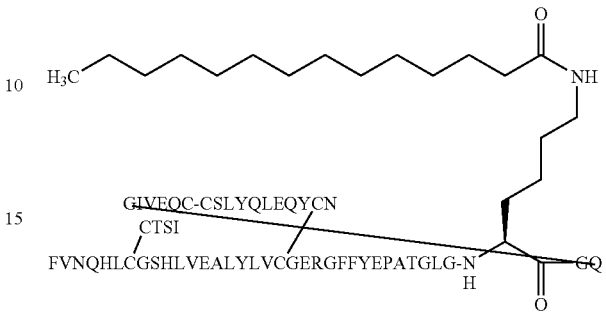

B(1-29)-B27E-B29A-TGLGKGQ-A(1-21)-A18Q Human insulin (SEQ ID NO:134) (117 mg, 20 μmol) was dissolved in aqueous sodium carbonate (100 mM, 2.5 mL) and added a solution of myristic acid N-hydroxysuccinimide ester (9 mg, may be prepared according to B. Faroux-Corlay et al., J. Med. Chem. 2001, 44, 2188-2203) in acetonitrile (1.8 mL). The resulting mixture was stirred at room temperature for 65 minutes. pH was adjusted to 5.5 with 1N hydrochloric acid. The solid formed was isolated by centrifugation and decantation. The residue was purified by preparative HPLC on a Macherey-Nagel SP 250/21 Nucleusil 300-7 C4 column, using a flow of 10 mL/min with the following gradient:

| 0-10 min: | 20% CH$_3$CN + 0.1% TFA, |
|---|---|
| 10-80 min: | 20%-90% CH$_3$CN + 0.1% TFA, |
| 35.0-45.0 min: | 50%-90% CH$_3$CN + 0.1% TFA. |

Pure fractions were pooled and lyophilised to afford 20 mg of the title compound.

MALDI-TOF MS: m/z=6509. Calculated: 6518

HPLC: Rt=11.64 min. Column: "Phenomenex, Jupiter", C4 5μ, 150×4_60 mm, injection: 20 μl. Solvents: A: 80% 0.0125 M Tris, 0.0187 M (NH$_4$)$_2$SO$_4$ pH=7, 20% CH$_3$CN; B: 80% CH$_3$CN, 20% water, flow 1.5 ml/min with the following gradient:

| 0-20 min: | 5-55% B, |
|---|---|
| 20-22 min: | 55-80% B, |
| 22-24 min: | 80% B, |
| 24-25 min: | 80-5% B, |
| 25-32 min: | 5% B. |

HPLC: Rt=12.95 min. Column: "Phenomenex, Jupiter", C4 5μ, 150×4_60 mm, injection: 20 μl. Solvents: A: 0.1% TFA, 10% CH$_3$CN, 89.9% water; B: 0.1% TFA, 80% CH$_3$CN, 19.9% water, flow: 1.5 ml/min with the following gradient:

| 0-17 min: | 20-90% B, |
|---|---|
| 17-21 min: | 90% B, |
| 21-23 min: | 90-20% B, |
| 23-30 min: | 20% B. |

Example 6

B(1-29)-B29A-TGLGK((eps)myristoyl)GQ-A(1-21)-A18Q Human insulin (SEQ ID NO:135) (PAK1837)

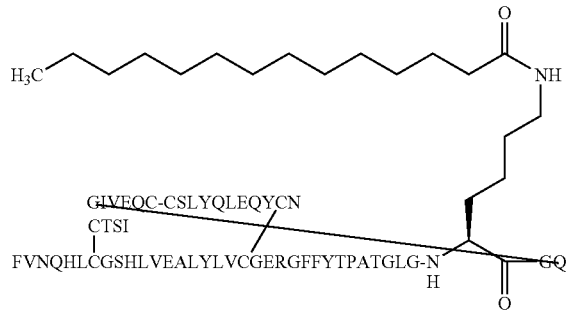

B(1-29)-B29A-TGLGKGQ-A(1-21)-A18Q Human insulin (SEQ ID NO:135) (151 mg, 24 µmol) was dissolved in aqueous sodium carbonate (100 mM, 5 mL) and added a solution of myristic acid N-hydroxysuccinimide ester (8 mg, may be prepared according to B. Faroux-Corlay et al., J. Med. Chem. 2001, 44, 2188-2203) in N-methylpyrrolidin-2-one (2.5 mL). The resulting mixture was stirred at room temperature for 45 minutes. pH was adjusted to 5.6 with 1N hydrochloric acid. The solid formed was isolated by centrifugation and decantation. The residue was purified by preparative HPLC on a Macherey-Nagel SP 250/21 Nucleusil 300-7 C4 column, using a flow of 8 mL/min with the following gradient:

| 0-5 min: | 10% CH$_3$CN + 0.1% TFA, |
|---|---|
| 5-35 min: | 10%-90% CH3CN + 0.1% TFA, |
| 35-40 min: | 90% CH$_3$CN + 0.1% TFA, |
| 40-45 min: | 100% CH$_3$CN. |

Pure fractions were pooled and lyophilised to afford 24 mg of the title compound.

MALDI-TOF MS: m/z=6489. Calculated: 6498

HPLC: Rt=10.97 min. Column: VYDAC Protein, C4 25 cm, cat #214TP54, injection: 5 µl. Solvents: A: 80% 0.01 M Tris, 0.015 M (NH$_4$)$_2$SO$_4$ pH=7.3, 20% CH$_3$CN; B: 80% CH$_3$CN, 20% water, flow 1.5 ml/min with the following gradient:

| 0-20 min: | 10-80% B, |
|---|---|
| 20-20.1 min: | 80-90% B, |
| 20.1-21 min: | 90-10% B, |
| 21-25 min: | 10% B. |

HPLC: Rt=13.09 min. Column: "Phenomenex, Jupiter", C4 5µ, 150×4_60 mm, injection: 25 µl. Solvents: A: 0.1% TFA, 10% CH$_3$CN, 89.9% water; B: 0.1% TFA, 80% CH$_3$CN, 19.9% water, flow: 1.5 ml/min with the following gradient:

| 0-17 min: | 20-90% B, |
|---|---|
| 17-21 min: | 90% B, |
| 21-23 min: | 90-20% B, |
| 23-30 min: | 20% B. |

Affinity to the human insulin receptor

| Example | IC$_{50}$ relative to human insulin in %. |
|---|---|
| 2 | 2% |
| 3 | 0.1% |
| 4 | 0.7% |

Pharmacological Methods

Assay (I)

Insulin receptor binding of the single-chain insulins of the invention.

The affinity of the single-chain insulins the invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM MgSO4, 0.025% Tween-20). Reagent mix for a single Packard Optiplate (Packard No. 6005190) is composed of 2.4 µl of a 1:5000 diluted purified recombinant human insulin receptor—exon 11, an amount of a stock solution of A14 Tyr[125I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl was then added and a dilution series is made from appropriate samples. To the dilution series was then added 100 µl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

Preparation of Monoclonal mIr Antibodies

Specific antibodies (F12) were produced by monoclonal technique: RBF mice were immunized by injecting 50 µg of purified mIR in FCA subcutaneously followed by two injections with 20 µg of mIR in FIA. High responder mice were boosted intravenously with 25 µg of mIR and the spleens were harvested after 3 days. Spleen cells were fused with the myeloma Fox cell line (Köhler, G & Milstein C. (1976), European J. Immunology, 6:511-19; Taggart R T et al (1983), Science 219:1228-30). Supernatants were screened for antibody production in a mIR specific ELISA. Positive wells were cloned and tested in Western blotting.

Assay (II)

Alternatively the insulin receptor binding was tested in a hIRBHK membrane assay as follows:

Binding of [$^{125}$I]-human insulin to membrane-associated recombinant human insulin receptor isoform A (hIR-A)

Reagents:

$^{125}$I-Insulin: Novo Nordisk A/S, mono $^{125}$I-(TyrA14) human insulin

Human Insulin: Novo Nordisk A/S,

Human serum albumin: Dade Behring, ORHA 194 C30, lot 455077

Plastic ware: Packard OptiPlate™-96, #6,005,290

Scintillant: Amersham Biosciences, WGA coated PVT microspheres, # RPNQ0001

Cells: BHK tk⁻ ts13 cells expressing recombinant human insulin receptor isoform A (hIR12-14).

Extraction of membrane-associated insulin receptors: BHK cells from a ten-layer cell factory were harvested and homogenised in 25 ml of ice-cold buffer (25 mM HEPES pH 7.4, 2.5 mM CaCl$_2$, 1 mM MgCl$_2$, 250 mg/l bacitracin, 0.1 mM Pefablock). The homogenate was layered carefully on 41% sucrose cushions, centrifuged in the ultracentrifuge at 95,000×g for 75 minutes in a Beckman SW28 rotor at 4° C. The plasma membranes were collected from the top of the sucrose cushion, diluted 1:4 with buffer and centrifuged at 40,000×g for 45 min in a Beckman SW28 rotor. The pellets were suspended in buffer (25 mM HEPES pH 7.4, 2.5 mM CaCl$_2$, 1 mM MgCl$_2$, 250 mg/l bacitracin, 0.1 mM Pefablock) and stored at −80° C.

Radioligand binding to membrane-associated insulin receptors was performed in duplicate in 96-well OptiPlates. Membrane protein was incubated for 150 minutes at 25° C. with 50 µM [$^{125}$I-Tyr$^{A14}$]-human insulin in a total volume of 200 ml assay buffer (50 mM HEPES, 150 mM NaCl, 5 mM MgSO$_4$, 0.01% Triton X-100, 0.1% HSA, Complete™ EDTA-free protease inhibitors) and increasing concentrations of human insulin or insulin analogues (typically between 0.01 and 300 nM). The assay was terminated by addition of 50 µl of a suspension of WGA-coated PVT microspheres (20 mg/ml). Following 5 minutes of slight agitation, the plate was centrifuged at 1500 RPM for 6 minutes, and bound radioactivity quantified by counting in a Packard TopCount NXT after a delay of 60 minutes.

Results are given as IC$_{50}$ relative to human insulin in %.

Assay (III)

Potency of the single-chain insulin derivatives of the invention relative to human insulin.

Wistar rats were used for testing the blood glucose lower efficacy of SCI af I.V bolus administration. Following administration the of either SCI or human insulin the concentration of blood glucose is monitored Assay (IV)

Determination in pigs of T50% of the single-chain insulins of the invention.

T50% is the time when 50% of an injected amount of the A14 Tyr[125I] labelled derivative of an insulin to be tested has disappeared from the injection site as measured with an external γ-counter.

The principles of laboratory animal care are followed, Specific pathogen-free LYYD, non-diabetic female pigs, crossbreed of Danish Landrace, Yorkshire and Duroc, were used (Holmenlund, Haarloev, Denmark) for pharmacokinetic and pharmacodynamic studies. The pigs are conscious, 4-5 months of age and weighing 70-95 kg. The animals are fasted overnight for 18 h before the experiment.

Formulated preparations of insulin derivatives labelled in TyrA14 with 125I are injected sc. in pigs as previously described (Ribel, U., Jørgensen, K, Brange, J, and Henriksen, U. The pig as a model for subcutaneous insulin absorption in man. Serrano-Rios, M. and Lefèbvre, P. J. 891-896. 1985. Amsterdam; New York; Oxford, Elsevier Science Publishers. 1985 (Conference Proceeding)).

At the beginning of the experiments a dose of 60 nmol of the insulin derivative according to the invention (test compound) and a dose of 60 nmol of insulin (both 125I labelled in Tyr A14) are injected at two separate sites in the neck of each pig.

The disappearance of the radioactive label from the site of sc. Injection is monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it is possible to measure continuously the disappearance of radioactivity from a subcutaneous depot for several days using cordless portable device (Scancys Laboratorieteknik, Vaerløse, DK-3500, Denmark). The measurements are performed at 1-min intervals, and the counted values are corrected for background activity.

IGF-1 Receptor Binding

IGF-1 receptor binding of the single-chain insulin was determined using a by a SPA assay (Scintillation Proximity Assay) microtiterplate antibody capture assay similar to that used for determining the Insulin receptor binding of the insulin derivatives of the invention, with the exception that the IGF1 receptor was used in stead of the insulin receptor, [125I]-human IGF-1 in stead of [125I]-human insulin and an antibody with specificity for the IGF-1 receptor.

The invention claimed is:

1. A polynucleotide encoding a single-chain insulin polypeptide having the formula:

B(1-26)-$X_1$-$X_2$-$X_3$-$X_4$-A(1-21)

wherein $X_1$ is Thr, Lys, or Arg; $X_2$ is Pro, Lys, or Asp; $X_3$ is Lys, Pro, or Glu; $X_4$ is a peptide sequence selected from the group consisting of AGRGSGK (SEQ ID NO: 15); AGLGSGK (SEQ ID NO: 33); AGMGSGK (SEQ ID NO: 45); ASWGSGK (SEQ ID NO: 48); TGLGSGQ (SEQ ID NO: 22); TGLGRGK (SEQ ID NO: 23); TGLGSGK (SEQ ID NO: 21); HGLYSGK (SEQ ID NO: 50); KGLGSGQ (SEQ ID NO: 51); VGLMSGK (SEQ ID NO: 56); VGLSSGQ (SEQ ID NO: 27); VGLYSGK (SEQ ID NO: 28), VGLSSGK (SEQ ID NO: 30); VGMSSGK (SEQ ID NO: 65); VWSSSGK (SEQ ID NO: 76), VGSSSGK (SEQ ID NO: 16) and VGMSSGK (SEQ ID NO: 106), wherein B(1-26) is a peptide chain consisting of the first 26 amino acid residues of the B chain of human insulin counted from the N-terminal end of the B chain or an analogue or derivative thereof, and A(1-21) is the natural insulin A chain or an analogue thereof or derivative thereof.

2. An expression vector comprising a polynucleotide according to claim 1.

3. A host cell transformed by an expression vector according to claim 2.

4. The polynucleotide of claim 1, wherein $X_1$ is Thr; $X_2$ is Pro; and $X_3$ is Lys.

5. An expression vector comprising a polynucleotide according to claim 4.

6. A host cell transformed by an expression vector according to claim 5.

7. A polynucleotide encoding a single-chain insulin polypeptide having the formula:

B(1-26)-$X_1$-$X_2$-$X_3$-$X_4$-A(1-21)

wherein $X_1$ is Thr; $X_2$ is Pro; $X_3$ is Lys; X4 is TGLGSGK (SEQ ID NO:21), wherein B(1-26) is a peptide chain consisting of the first 26 amino acid residues of the B chain of human insulin counted from the N-terminal end of the B chain or an analogue or derivative thereof, and A(1-21) is the natural insulin A chain or an analogue thereof or derivative thereof.

8. An expression vector comprising a polynucleotide according to claim 7.

9. A host cell transformed by an expression vector according to claim 8.

10. A single-chain insulin polypeptide having the formula:

B(1-26)-$X_1$-$X_2$-$X_3$-$X_4$-A(1-21)

wherein $X_1$ is Thr, Lys, or Arg; $X_2$ is Pro, Lys, or Asp; $X_3$ is Lys, Pro, or Glu; $X_4$ is a peptide sequence selected from the group consisting of AGRGSGK (SEQ ID NO: 15); AGLGSGK (SEQ ID NO: 33); AGMGSGK (SEQ ID NO: 45); ASWGSGK (SEQ ID NO: 48); TGLGSGQ (SEQ ID NO: 22); TGLGRGK (SEQ ID NO: 23);

TGLGSGK (SEQ ID NO: 21); HGLYSGK (SEQ ID NO: 50); KGLGSGQ (SEQ ID NO: 51); VGLMSGK (SEQ ID NO: 56); VGLSSGQ (SEQ ID NO: 27); VGLYSGK (SEQ ID NO: 28), VGLSSGK (SEQ ID NO: 30); VGMSSGK (SEQ ID NO: 65); VWSSSGK (SEQ ID NO: 76), VGSSSGK (SEQ ID NO: 16) and VGMSSGK (SEQ ID NO: 106),
wherein B(1-26) is a peptide chain consisting of the first 26 amino acid residues of the B chain of human insulin counted from the N-terminal end of the B chain or an analogue or derivative thereof, and A(1-21) is the natural insulin A chain or an analogue thereof or derivative thereof.

11. The single-chain insulin polypeptide of claim 10, wherein $X_1$ is Thr; $X_2$ is Pro; and $X_3$ is Lys.

12. A pharmaceutical composition comprising the single chain insulin polypeptide of claim 11 and a pharmaceutically acceptable excipient.

13. A method for treating type 1 diabetes or type 2 diabetes comprising administering the pharmaceutical composition of claim 12 to a subject in need thereof.

14. The single-chain insulin polypeptide of claim 10, wherein $X_1$ is Thr; $X_2$ is Pro; $X_3$ is Lys; and X4 is TGLGSGK (SEQ ID NO:21).

15. A pharmaceutical composition comprising the single chain insulin polypeptide of claim 14 and a pharmaceutically acceptable excipient.

16. A method for treating type 1 diabetes or type 2 diabetes comprising administering the pharmaceutical composition of claim 15 to a subject in need thereof.

17. A pharmaceutical composition comprising the single chain insulin polypeptide of claim 10 and a pharmaceutically acceptable excipient.

18. A method for treating type 1 diabetes or type 2 diabetes comprising administering the pharmaceutical composition of claim 17 to a subject in need thereof.

* * * * *

SEQUENCE LISTING

```
<160> NUMBER OF SEQ ID NOS: 135

<210> SEQ ID NO 1
<211> LENGTH: 7
<212> TYPE: PRT
<213> ORGANISM: Artificial
<220> FEATURE:
<223> OTHER INFORMATION: synthetic

<400> SEQUENCE: 1

Gly Gly Gly Pro Gly Lys Arg
1               5

<210> SEQ ID NO 2
<211> LENGTH: 7
<212> TYPE: PRT
<213> ORGANISM: Artificial
<220> FEATURE:
<223> OTHER INFORMATION: synthetic

<400> SEQUENCE: 2

Arg Arg Gly Pro Gly Gly Gly
1               5
```

```
<210> SEQ ID NO 3
<211> LENGTH: 7
<212> TYPE: PRT
<213> ORGANISM: Artificial
<220> FEATURE:
<223> OTHER INFORMATION: synthetic

<400> SEQUENCE: 3

Gly Gly Gly Gly Gly Lys Arg
1               5

<210> SEQ ID NO 4
<211> LENGTH: 7
<212> TYPE: PRT
<213> ORGANISM: Artificial
<220> FEATURE:
<223> OTHER INFORMATION: synthetic

<400> SEQUENCE: 4

Arg Arg Gly Gly Gly Gly Gly
1               5

<210> SEQ ID NO 5
<211> LENGTH: 9
<212> TYPE: PRT
<213> ORGANISM: Artificial
<220> FEATURE:
<223> OTHER INFORMATION: synthetic

<400> SEQUENCE: 5

Gly Gly Ala Pro Gly Asp Val Lys Arg
1               5

<210> SEQ ID NO 6
<211> LENGTH: 9
<212> TYPE: PRT
<213> ORGANISM: Artificial
<220> FEATURE:
<223> OTHER INFORMATION: synthetic

<400> SEQUENCE: 6

Arg Arg Ala Pro Gly Asp Val Gly Gly
1               5

<210> SEQ ID NO 7
<211> LENGTH: 9
<212> TYPE: PRT
<213> ORGANISM: Artificial
<220> FEATURE:
<223> OTHER INFORMATION: synthetic

<400> SEQUENCE: 7

Gly Gly Tyr Pro Gly Asp Val Lys Arg
1               5

<210> SEQ ID NO 8
<211> LENGTH: 9
<212> TYPE: PRT
<213> ORGANISM: Artificial
<220> FEATURE:
<223> OTHER INFORMATION: synthetic

<400> SEQUENCE: 8

Arg Arg Tyr Pro Gly Asp Val Gly Gly
1               5
```

```
<210> SEQ ID NO 9
<211> LENGTH: 9
<212> TYPE: PRT
<213> ORGANISM: Artificial
<220> FEATURE:
<223> OTHER INFORMATION: synthetic

<400> SEQUENCE: 9

Gly Gly His Pro Gly Asp Val Lys Arg
1               5

<210> SEQ ID NO 10
<211> LENGTH: 9
<212> TYPE: PRT
<213> ORGANISM: Artificial
<220> FEATURE:
<223> OTHER INFORMATION: synthetic

<400> SEQUENCE: 10

Arg Arg His Pro Gly Asp Val Gly Gly
1               5

<210> SEQ ID NO 11
<211> LENGTH: 12
<212> TYPE: PRT
<213> ORGANISM: Artificial
<220> FEATURE:
<223> OTHER INFORMATION: synthetic

<400> SEQUENCE: 11

Gln Pro Leu Ala Leu Glu Gly Ser Leu Gln Lys Arg
1               5                   10

<210> SEQ ID NO 12
<211> LENGTH: 12
<212> TYPE: PRT
<213> ORGANISM: Artificial
<220> FEATURE:
<223> OTHER INFORMATION: synthetic

<400> SEQUENCE: 12

Gly Tyr Gly Ser Ser Ser Arg Arg Ala Pro Gln Thr
1               5                   10

<210> SEQ ID NO 13
<211> LENGTH: 11
<212> TYPE: PRT
<213> ORGANISM: Artificial
<220> FEATURE:
<223> OTHER INFORMATION: synthetic

<400> SEQUENCE: 13

Gly Tyr Gly Ser Ser Ser Arg Arg Ala Pro Gln
1               5                   10

<210> SEQ ID NO 14
<211> LENGTH: 12
<212> TYPE: PRT
<213> ORGANISM: Artificial
<220> FEATURE:
<223> OTHER INFORMATION: synthetic

<400> SEQUENCE: 14

Gly Tyr Gly Ser Ser Ser Ala Ala Ala Pro Gln Thr
1               5                   10

<210> SEQ ID NO 15
```

```
<211> LENGTH: 7
<212> TYPE: PRT
<213> ORGANISM: Artificial
<220> FEATURE:
<223> OTHER INFORMATION: synthetic

<400> SEQUENCE: 15

Ala Gly Arg Gly Ser Gly Lys
1               5

<210> SEQ ID NO 16
<211> LENGTH: 7
<212> TYPE: PRT
<213> ORGANISM: Artificial
<220> FEATURE:
<223> OTHER INFORMATION: synthetic

<400> SEQUENCE: 16

Val Gly Ser Ser Ser Gly Lys
1               5

<210> SEQ ID NO 17
<211> LENGTH: 7
<212> TYPE: PRT
<213> ORGANISM: Artificial
<220> FEATURE:
<223> OTHER INFORMATION: synthetic

<400> SEQUENCE: 17

Val Gly Ser Ser Arg Gly Lys
1               5

<210> SEQ ID NO 18
<211> LENGTH: 7
<212> TYPE: PRT
<213> ORGANISM: Artificial
<220> FEATURE:
<223> OTHER INFORMATION: synthetic

<400> SEQUENCE: 18

Ala Gly Arg Gly Ser Gly Pro
1               5

<210> SEQ ID NO 19
<211> LENGTH: 7
<212> TYPE: PRT
<213> ORGANISM: Artificial
<220> FEATURE:
<223> OTHER INFORMATION: synthetic

<400> SEQUENCE: 19

Thr Gly Leu Gly Lys Gly Gln
1               5

<210> SEQ ID NO 20
<211> LENGTH: 7
<212> TYPE: PRT
<213> ORGANISM: Artificial
<220> FEATURE:
<223> OTHER INFORMATION: synthetic

<400> SEQUENCE: 20

Thr Gly Leu Gly Lys Gly Arg
1               5

<210> SEQ ID NO 21
<211> LENGTH: 7
```

```
<212> TYPE: PRT
<213> ORGANISM: Artificial
<220> FEATURE:
<223> OTHER INFORMATION: synthetic

<400> SEQUENCE: 21

Thr Gly Leu Gly Ser Gly Lys
1               5

<210> SEQ ID NO 22
<211> LENGTH: 7
<212> TYPE: PRT
<213> ORGANISM: Artificial
<220> FEATURE:
<223> OTHER INFORMATION: synthetic

<400> SEQUENCE: 22

Thr Gly Leu Gly Ser Gly Gln
1               5

<210> SEQ ID NO 23
<211> LENGTH: 7
<212> TYPE: PRT
<213> ORGANISM: Artificial
<220> FEATURE:
<223> OTHER INFORMATION: synthetic

<400> SEQUENCE: 23

Thr Gly Leu Gly Arg Gly Lys
1               5

<210> SEQ ID NO 24
<211> LENGTH: 7
<212> TYPE: PRT
<213> ORGANISM: Artificial
<220> FEATURE:
<223> OTHER INFORMATION: synthetic

<400> SEQUENCE: 24

Ala Gly Leu Gly Ser Gly Lys
1               5

<210> SEQ ID NO 25
<211> LENGTH: 7
<212> TYPE: PRT
<213> ORGANISM: Artificial
<220> FEATURE:
<223> OTHER INFORMATION: synthetic

<400> SEQUENCE: 25

Ala Gly Met Gly Ser Gly Pro
1               5

<210> SEQ ID NO 26
<211> LENGTH: 8
<212> TYPE: PRT
<213> ORGANISM: Artificial
<220> FEATURE:
<223> OTHER INFORMATION: synthetic

<400> SEQUENCE: 26

Val Ala Gly Met Gly Ser Gly Pro
1               5

<210> SEQ ID NO 27
<211> LENGTH: 7
<212> TYPE: PRT
```

```
<213> ORGANISM: Artificial
<220> FEATURE:
<223> OTHER INFORMATION: synthetic

<400> SEQUENCE: 27

Val Gly Leu Ser Ser Gly Gln
1               5

<210> SEQ ID NO 28
<211> LENGTH: 7
<212> TYPE: PRT
<213> ORGANISM: Artificial
<220> FEATURE:
<223> OTHER INFORMATION: synthetic

<400> SEQUENCE: 28

Val Gly Leu Tyr Ser Gly Lys
1               5

<210> SEQ ID NO 29
<211> LENGTH: 11
<212> TYPE: PRT
<213> ORGANISM: Artificial
<220> FEATURE:
<223> OTHER INFORMATION: synthetic

<400> SEQUENCE: 29

Val Gly Leu Gly Gly Gly Pro Gly Ala Gly Lys
1               5                   10

<210> SEQ ID NO 30
<211> LENGTH: 7
<212> TYPE: PRT
<213> ORGANISM: Artificial
<220> FEATURE:
<223> OTHER INFORMATION: synthetic

<400> SEQUENCE: 30

Val Gly Leu Ser Ser Gly Lys
1               5

<210> SEQ ID NO 31
<211> LENGTH: 7
<212> TYPE: PRT
<213> ORGANISM: Artificial
<220> FEATURE:
<223> OTHER INFORMATION: synthetic

<400> SEQUENCE: 31

Val Gly Arg Ser Ser Gly Lys
1               5

<210> SEQ ID NO 32
<211> LENGTH: 5
<212> TYPE: PRT
<213> ORGANISM: Artificial
<220> FEATURE:
<223> OTHER INFORMATION: synthetic

<400> SEQUENCE: 32

Ala Gly Arg Gly Lys
1               5

<210> SEQ ID NO 33
<211> LENGTH: 7
<212> TYPE: PRT
<213> ORGANISM: Artificial
```

```
<220> FEATURE:
<223> OTHER INFORMATION: synthetic

<400> SEQUENCE: 33

Ala Gly Leu Gly Ser Gly Lys
1               5

<210> SEQ ID NO 34
<211> LENGTH: 6
<212> TYPE: PRT
<213> ORGANISM: Artificial
<220> FEATURE:
<223> OTHER INFORMATION: synthetic

<400> SEQUENCE: 34

Arg Ser Phe Asp Gly Lys
1               5

<210> SEQ ID NO 35
<211> LENGTH: 8
<212> TYPE: PRT
<213> ORGANISM: Artificial
<220> FEATURE:
<223> OTHER INFORMATION: synthetic

<400> SEQUENCE: 35

Thr Val Gly Ser Ser Arg Gly Lys
1               5

<210> SEQ ID NO 36
<211> LENGTH: 7
<212> TYPE: PRT
<213> ORGANISM: Artificial
<220> FEATURE:
<223> OTHER INFORMATION: synthetic

<400> SEQUENCE: 36

Thr Gly Ser Ser Arg Gly Lys
1               5

<210> SEQ ID NO 37
<211> LENGTH: 7
<212> TYPE: PRT
<213> ORGANISM: Artificial
<220> FEATURE:
<223> OTHER INFORMATION: synthetic

<400> SEQUENCE: 37

Ala Gly Leu Gly Asp Gly Lys
1               5

<210> SEQ ID NO 38
<211> LENGTH: 7
<212> TYPE: PRT
<213> ORGANISM: Artificial
<220> FEATURE:
<223> OTHER INFORMATION: synthetic

<400> SEQUENCE: 38

Ala Gly Leu Gly Val Gly Lys
1               5

<210> SEQ ID NO 39
<211> LENGTH: 7
<212> TYPE: PRT
<213> ORGANISM: Artificial
<220> FEATURE:
```

<223> OTHER INFORMATION: synthetic

<400> SEQUENCE: 39

Ala Gly Leu Gly Met Gly Lys
1               5

<210> SEQ ID NO 40
<211> LENGTH: 7
<212> TYPE: PRT
<213> ORGANISM: Artificial
<220> FEATURE:
<223> OTHER INFORMATION: synthetic

<400> SEQUENCE: 40

Ala Gly Leu Gly Tyr Gly Lys
1               5

<210> SEQ ID NO 41
<211> LENGTH: 7
<212> TYPE: PRT
<213> ORGANISM: Artificial
<220> FEATURE:
<223> OTHER INFORMATION: synthetic

<400> SEQUENCE: 41

Ala Gly Leu Gly Gln Gly Lys
1               5

<210> SEQ ID NO 42
<211> LENGTH: 7
<212> TYPE: PRT
<213> ORGANISM: Artificial
<220> FEATURE:
<223> OTHER INFORMATION: synthetic

<400> SEQUENCE: 42

Ala Gly Leu Gly Gly Gly Lys
1               5

<210> SEQ ID NO 43
<211> LENGTH: 7
<212> TYPE: PRT
<213> ORGANISM: Artificial
<220> FEATURE:
<223> OTHER INFORMATION: synthetic

<400> SEQUENCE: 43

Ala Gly Leu Gly Arg Gly Lys
1               5

<210> SEQ ID NO 44
<211> LENGTH: 7
<212> TYPE: PRT
<213> ORGANISM: Artificial
<220> FEATURE:
<223> OTHER INFORMATION: synthetic

<400> SEQUENCE: 44

Ala Gly Leu Gly Ser Gly Gln
1               5

<210> SEQ ID NO 45
<211> LENGTH: 7
<212> TYPE: PRT
<213> ORGANISM: Artificial
<220> FEATURE:
<223> OTHER INFORMATION: synthetic

```
<400> SEQUENCE: 45

Ala Gly Met Gly Ser Gly Lys
1               5

<210> SEQ ID NO 46
<211> LENGTH: 7
<212> TYPE: PRT
<213> ORGANISM: Artificial
<220> FEATURE:
<223> OTHER INFORMATION: synthetic

<400> SEQUENCE: 46

Ala Gly Ser Ser Ser Gly Lys
1               5

<210> SEQ ID NO 47
<211> LENGTH: 7
<212> TYPE: PRT
<213> ORGANISM: Artificial
<220> FEATURE:
<223> OTHER INFORMATION: synthetic

<400> SEQUENCE: 47

Trp Ala Ser Gly Ser Gly Lys
1               5

<210> SEQ ID NO 48
<211> LENGTH: 7
<212> TYPE: PRT
<213> ORGANISM: Artificial
<220> FEATURE:
<223> OTHER INFORMATION: synthetic

<400> SEQUENCE: 48

Ala Ser Trp Gly Ser Gly Lys
1               5

<210> SEQ ID NO 49
<211> LENGTH: 7
<212> TYPE: PRT
<213> ORGANISM: Artificial
<220> FEATURE:
<223> OTHER INFORMATION: synthetic

<400> SEQUENCE: 49

Ala Trp Ser Gly Ser Gly Lys
1               5

<210> SEQ ID NO 50
<211> LENGTH: 7
<212> TYPE: PRT
<213> ORGANISM: Artificial
<220> FEATURE:
<223> OTHER INFORMATION: synthetic

<400> SEQUENCE: 50

His Gly Leu Tyr Ser Gly Lys
1               5

<210> SEQ ID NO 51
<211> LENGTH: 7
<212> TYPE: PRT
<213> ORGANISM: Artificial
<220> FEATURE:
<223> OTHER INFORMATION: synthetic
```

```
<400> SEQUENCE: 51

Lys Gly Leu Gly Ser Gly Gln
1               5

<210> SEQ ID NO 52
<211> LENGTH: 6
<212> TYPE: PRT
<213> ORGANISM: Artificial
<220> FEATURE:
<223> OTHER INFORMATION: synthetic

<400> SEQUENCE: 52

Gly Arg Gly Ser Gly Lys
1               5

<210> SEQ ID NO 53
<211> LENGTH: 7
<212> TYPE: PRT
<213> ORGANISM: Artificial
<220> FEATURE:
<223> OTHER INFORMATION: synthetic

<400> SEQUENCE: 53

Val Gly Leu Ser Ser Gly Asp
1               5

<210> SEQ ID NO 54
<211> LENGTH: 7
<212> TYPE: PRT
<213> ORGANISM: Artificial
<220> FEATURE:
<223> OTHER INFORMATION: synthetic

<400> SEQUENCE: 54

Val Gly Leu Ser Ser Gly Gln
1               5

<210> SEQ ID NO 55
<211> LENGTH: 7
<212> TYPE: PRT
<213> ORGANISM: Artificial
<220> FEATURE:
<223> OTHER INFORMATION: synthetic

<400> SEQUENCE: 55

Val Gly Leu Arg Ser Gly Lys
1               5

<210> SEQ ID NO 56
<211> LENGTH: 7
<212> TYPE: PRT
<213> ORGANISM: Artificial
<220> FEATURE:
<223> OTHER INFORMATION: synthetic

<400> SEQUENCE: 56

Val Gly Leu Met Ser Gly Lys
1               5

<210> SEQ ID NO 57
<211> LENGTH: 4
<212> TYPE: PRT
<213> ORGANISM: Artificial
<220> FEATURE:
<223> OTHER INFORMATION: synthetic

<400> SEQUENCE: 57
```

```
Gly Ser Gly Lys
1

<210> SEQ ID NO 58
<211> LENGTH: 9
<212> TYPE: PRT
<213> ORGANISM: Artificial
<220> FEATURE:
<223> OTHER INFORMATION: synthetic

<400> SEQUENCE: 58

Val Gly Leu Gly Pro Gly Ala Gly Lys
1               5

<210> SEQ ID NO 59
<211> LENGTH: 10
<212> TYPE: PRT
<213> ORGANISM: Artificial
<220> FEATURE:
<223> OTHER INFORMATION: synthetic

<400> SEQUENCE: 59

Val Gly Leu Gly Gly Gly Pro Gly Ala Gly
1               5                   10

<210> SEQ ID NO 60
<211> LENGTH: 10
<212> TYPE: PRT
<213> ORGANISM: Artificial
<220> FEATURE:
<223> OTHER INFORMATION: synthetic

<400> SEQUENCE: 60

Val Gly Leu Gly Gly Pro Gly Ala Gly Lys
1               5                   10

<210> SEQ ID NO 61
<211> LENGTH: 11
<212> TYPE: PRT
<213> ORGANISM: Artificial
<220> FEATURE:
<223> OTHER INFORMATION: synthetic

<400> SEQUENCE: 61

Val Gly Leu Gly Lys Gly Pro Gly Ala Gly Lys
1               5                   10

<210> SEQ ID NO 62
<211> LENGTH: 7
<212> TYPE: PRT
<213> ORGANISM: Artificial
<220> FEATURE:
<223> OTHER INFORMATION: synthetic

<400> SEQUENCE: 62

His Gly Arg Gly Ser Gly Lys
1               5

<210> SEQ ID NO 63
<211> LENGTH: 7
<212> TYPE: PRT
<213> ORGANISM: Artificial
<220> FEATURE:
<223> OTHER INFORMATION: synthetic

<400> SEQUENCE: 63
```

Lys Gly Leu Ser Ser Gly Gln
1               5

<210> SEQ ID NO 64
<211> LENGTH: 7
<212> TYPE: PRT
<213> ORGANISM: Artificial
<220> FEATURE:
<223> OTHER INFORMATION: synthetic

<400> SEQUENCE: 64

Val Lys Leu Ser Ser Gly Gln
1               5

<210> SEQ ID NO 65
<211> LENGTH: 7
<212> TYPE: PRT
<213> ORGANISM: Artificial
<220> FEATURE:
<223> OTHER INFORMATION: synthetic

<400> SEQUENCE: 65

Val Gly Met Ser Ser Gly Lys
1               5

<210> SEQ ID NO 66
<211> LENGTH: 7
<212> TYPE: PRT
<213> ORGANISM: Artificial
<220> FEATURE:
<223> OTHER INFORMATION: synthetic

<400> SEQUENCE: 66

Thr Gly Ser Ser Ser Gly Lys
1               5

<210> SEQ ID NO 67
<211> LENGTH: 8
<212> TYPE: PRT
<213> ORGANISM: Artificial
<220> FEATURE:
<223> OTHER INFORMATION: synthetic

<400> SEQUENCE: 67

Thr Val Gly Ser Ser Ser Gly Lys
1               5

<210> SEQ ID NO 68
<211> LENGTH: 7
<212> TYPE: PRT
<213> ORGANISM: Artificial
<220> FEATURE:
<223> OTHER INFORMATION: synthetic

<400> SEQUENCE: 68

Leu Gly Ser Ser Ser Gly Lys
1               5

<210> SEQ ID NO 69
<211> LENGTH: 7
<212> TYPE: PRT
<213> ORGANISM: Artificial
<220> FEATURE:
<223> OTHER INFORMATION: synthetic

<400> SEQUENCE: 69

Arg Gly Ser Ser Ser Gly Lys 1               5

<210> SEQ ID NO 70
<211> LENGTH: 7
<212> TYPE: PRT
<213> ORGANISM: Artificial
<220> FEATURE:
<223> OTHER INFORMATION: synthetic

<400> SEQUENCE: 70

Gln Gly Ser Ser Ser Gly Lys
1               5

<210> SEQ ID NO 71
<211> LENGTH: 7
<212> TYPE: PRT
<213> ORGANISM: Artificial
<220> FEATURE:
<223> OTHER INFORMATION: synthetic

<400> SEQUENCE: 71

Gly Gly Ser Ser Ser Gly Lys
1               5

<210> SEQ ID NO 72
<211> LENGTH: 7
<212> TYPE: PRT
<213> ORGANISM: Artificial
<220> FEATURE:
<223> OTHER INFORMATION: synthetic

<400> SEQUENCE: 72

Ser Gly Ser Ser Ser Gly Lys
1               5

<210> SEQ ID NO 73
<211> LENGTH: 7
<212> TYPE: PRT
<213> ORGANISM: Artificial
<220> FEATURE:
<223> OTHER INFORMATION: synthetic

<400> SEQUENCE: 73

Val Asp Ser Ser Ser Gly Lys
1               5

<210> SEQ ID NO 74
<211> LENGTH: 7
<212> TYPE: PRT
<213> ORGANISM: Artificial
<220> FEATURE:
<223> OTHER INFORMATION: synthetic

<400> SEQUENCE: 74

Val Pro Ser Ser Ser Gly Lys
1               5

<210> SEQ ID NO 75
<211> LENGTH: 7
<212> TYPE: PRT
<213> ORGANISM: Artificial
<220> FEATURE:
<223> OTHER INFORMATION: synthetic

<400> SEQUENCE: 75

Val Glu Ser Ser Ser Gly Lys
1               5

```
<210> SEQ ID NO 76
<211> LENGTH: 7
<212> TYPE: PRT
<213> ORGANISM: Artificial
<220> FEATURE:
<223> OTHER INFORMATION: synthetic

<400> SEQUENCE: 76

Val Trp Ser Ser Ser Gly Lys
1               5

<210> SEQ ID NO 77
<211> LENGTH: 7
<212> TYPE: PRT
<213> ORGANISM: Artificial
<220> FEATURE:
<223> OTHER INFORMATION: synthetic

<400> SEQUENCE: 77

Val Thr Ser Ser Ser Gly Lys
1               5

<210> SEQ ID NO 78
<211> LENGTH: 7
<212> TYPE: PRT
<213> ORGANISM: Artificial
<220> FEATURE:
<223> OTHER INFORMATION: synthetic

<400> SEQUENCE: 78

Val Ala Ser Ser Ser Gly Lys
1               5

<210> SEQ ID NO 79
<211> LENGTH: 7
<212> TYPE: PRT
<213> ORGANISM: Artificial
<220> FEATURE:
<223> OTHER INFORMATION: synthetic

<400> SEQUENCE: 79

Val Ser Ser Ser Ser Gly Lys
1               5

<210> SEQ ID NO 80
<211> LENGTH: 7
<212> TYPE: PRT
<213> ORGANISM: Artificial
<220> FEATURE:
<223> OTHER INFORMATION: synthetic

<400> SEQUENCE: 80

Val Arg Ser Ser Ser Gly Lys
1               5

<210> SEQ ID NO 81
<211> LENGTH: 8
<212> TYPE: PRT
<213> ORGANISM: Artificial
<220> FEATURE:
<223> OTHER INFORMATION: synthetic

<400> SEQUENCE: 81

Gln Val Gly Ser Ser Ser Gly Lys
1               5
```

```
<210> SEQ ID NO 82
<211> LENGTH: 8
<212> TYPE: PRT
<213> ORGANISM: Artificial
<220> FEATURE:
<223> OTHER INFORMATION: synthetic

<400> SEQUENCE: 82

Glu Val Gly Ser Ser Ser Gly Lys
1               5

<210> SEQ ID NO 83
<211> LENGTH: 8
<212> TYPE: PRT
<213> ORGANISM: Artificial
<220> FEATURE:
<223> OTHER INFORMATION: synthetic

<400> SEQUENCE: 83

Ser Val Gly Ser Ser Ser Gly Lys
1               5

<210> SEQ ID NO 84
<211> LENGTH: 8
<212> TYPE: PRT
<213> ORGANISM: Artificial
<220> FEATURE:
<223> OTHER INFORMATION: synthetic

<400> SEQUENCE: 84

Leu Val Gly Ser Ser Ser Gly Lys
1               5

<210> SEQ ID NO 85
<211> LENGTH: 8
<212> TYPE: PRT
<213> ORGANISM: Artificial
<220> FEATURE:
<223> OTHER INFORMATION: synthetic

<400> SEQUENCE: 85

Pro Val Gly Ser Ser Ser Gly Lys
1               5

<210> SEQ ID NO 86
<211> LENGTH: 8
<212> TYPE: PRT
<213> ORGANISM: Artificial
<220> FEATURE:
<223> OTHER INFORMATION: synthetic

<400> SEQUENCE: 86

Val Val Gly Ser Ser Ser Gly Lys
1               5

<210> SEQ ID NO 87
<211> LENGTH: 8
<212> TYPE: PRT
<213> ORGANISM: Artificial
<220> FEATURE:
<223> OTHER INFORMATION: synthetic

<400> SEQUENCE: 87

Gly Val Gly Ser Ser Ser Gly Lys
1               5
```

```
<210> SEQ ID NO 88
<211> LENGTH: 6
<212> TYPE: PRT
<213> ORGANISM: Artificial
<220> FEATURE:
<223> OTHER INFORMATION: synthetic

<400> SEQUENCE: 88

Val Gly Ser Ser Gly Lys
1               5

<210> SEQ ID NO 89
<211> LENGTH: 7
<212> TYPE: PRT
<213> ORGANISM: Artificial
<220> FEATURE:
<223> OTHER INFORMATION: synthetic

<400> SEQUENCE: 89

Val Gly Ser Ser Ser Ala Lys
1               5

<210> SEQ ID NO 90
<211> LENGTH: 7
<212> TYPE: PRT
<213> ORGANISM: Artificial
<220> FEATURE:
<223> OTHER INFORMATION: synthetic

<400> SEQUENCE: 90

Val Gly His Ser Arg Gly Lys
1               5

<210> SEQ ID NO 91
<211> LENGTH: 7
<212> TYPE: PRT
<213> ORGANISM: Artificial
<220> FEATURE:
<223> OTHER INFORMATION: synthetic

<400> SEQUENCE: 91

His Gly Ser Ser Arg Gly Lys
1               5

<210> SEQ ID NO 92
<211> LENGTH: 7
<212> TYPE: PRT
<213> ORGANISM: Artificial
<220> FEATURE:
<223> OTHER INFORMATION: synthetic

<400> SEQUENCE: 92

Val Gly Ser Ala Ser Gly Lys
1               5

<210> SEQ ID NO 93
<211> LENGTH: 7
<212> TYPE: PRT
<213> ORGANISM: Artificial
<220> FEATURE:
<223> OTHER INFORMATION: synthetic

<400> SEQUENCE: 93

Val Gly Ser Asn Ser Gly Lys
1               5

<210> SEQ ID NO 94
```

```
<211> LENGTH: 7
<212> TYPE: PRT
<213> ORGANISM: Artificial
<220> FEATURE:
<223> OTHER INFORMATION: synthetic

<400> SEQUENCE: 94

Val Gly Ser Arg Ser Gly Lys
1               5

<210> SEQ ID NO 95
<211> LENGTH: 7
<212> TYPE: PRT
<213> ORGANISM: Artificial
<220> FEATURE:
<223> OTHER INFORMATION: synthetic

<400> SEQUENCE: 95

Val Gly Ser His Arg Gly Lys
1               5

<210> SEQ ID NO 96
<211> LENGTH: 7
<212> TYPE: PRT
<213> ORGANISM: Artificial
<220> FEATURE:
<223> OTHER INFORMATION: synthetic

<400> SEQUENCE: 96

Val Gly Ser Gly Ser Gly Lys
1               5

<210> SEQ ID NO 97
<211> LENGTH: 7
<212> TYPE: PRT
<213> ORGANISM: Artificial
<220> FEATURE:
<223> OTHER INFORMATION: synthetic

<400> SEQUENCE: 97

Val Gly Ser Tyr Ser Gly Lys
1               5

<210> SEQ ID NO 98
<211> LENGTH: 7
<212> TYPE: PRT
<213> ORGANISM: Artificial
<220> FEATURE:
<223> OTHER INFORMATION: synthetic

<400> SEQUENCE: 98

Val Gly Ser Met Ser Gly Lys
1               5

<210> SEQ ID NO 99
<211> LENGTH: 7
<212> TYPE: PRT
<213> ORGANISM: Artificial
<220> FEATURE:
<223> OTHER INFORMATION: synthetic

<400> SEQUENCE: 99

Val Gly Pro Ser Ser Gly Lys
1               5

<210> SEQ ID NO 100
<211> LENGTH: 7
```

-continued

<212> TYPE: PRT
<213> ORGANISM: Artificial
<220> FEATURE:
<223> OTHER INFORMATION: synthetic

<400> SEQUENCE: 100

Val Gly Thr Ser Ser Gly Lys
1               5

<210> SEQ ID NO 101
<211> LENGTH: 7
<212> TYPE: PRT
<213> ORGANISM: Artificial
<220> FEATURE:
<223> OTHER INFORMATION: synthetic

<400> SEQUENCE: 101

Val Gly Gln Ser Ser Gly Lys
1               5

<210> SEQ ID NO 102
<211> LENGTH: 7
<212> TYPE: PRT
<213> ORGANISM: Artificial
<220> FEATURE:
<223> OTHER INFORMATION: synthetic

<400> SEQUENCE: 102

Val Gly Tyr Ser Ser Gly Lys
1               5

<210> SEQ ID NO 103
<211> LENGTH: 7
<212> TYPE: PRT
<213> ORGANISM: Artificial
<220> FEATURE:
<223> OTHER INFORMATION: synthetic

<400> SEQUENCE: 103

Val Gly Lys Ser Ser Gly Lys
1               5

<210> SEQ ID NO 104
<211> LENGTH: 7
<212> TYPE: PRT
<213> ORGANISM: Artificial
<220> FEATURE:
<223> OTHER INFORMATION: synthetic

<400> SEQUENCE: 104

Val Gly Gly Ser Ser Gly Lys
1               5

<210> SEQ ID NO 105
<211> LENGTH: 7
<212> TYPE: PRT
<213> ORGANISM: Artificial
<220> FEATURE:
<223> OTHER INFORMATION: synthetic

<400> SEQUENCE: 105

Val Gly Arg Ser Ser Gly Lys
1               5

<210> SEQ ID NO 106
<211> LENGTH: 7
<212> TYPE: PRT

```
<213> ORGANISM: Artificial
<220> FEATURE:
<223> OTHER INFORMATION: synthetic

<400> SEQUENCE: 106

Val Gly Met Ser Ser Gly Lys
1               5

<210> SEQ ID NO 107
<211> LENGTH: 7
<212> TYPE: PRT
<213> ORGANISM: Artificial
<220> FEATURE:
<223> OTHER INFORMATION: synthetic

<400> SEQUENCE: 107

Val Gly Val Ser Ser Gly Lys
1               5

<210> SEQ ID NO 108
<211> LENGTH: 7
<212> TYPE: PRT
<213> ORGANISM: Artificial
<220> FEATURE:
<223> OTHER INFORMATION: synthetic

<400> SEQUENCE: 108

Val Gly His Ser Ser Gly Lys
1               5

<210> SEQ ID NO 109
<211> LENGTH: 5
<212> TYPE: PRT
<213> ORGANISM: Artificial
<220> FEATURE:
<223> OTHER INFORMATION: synthetic

<400> SEQUENCE: 109

Gly Ser Ser Gly Lys
1               5

<210> SEQ ID NO 110
<211> LENGTH: 6
<212> TYPE: PRT
<213> ORGANISM: Artificial
<220> FEATURE:
<223> OTHER INFORMATION: synthetic

<400> SEQUENCE: 110

Gln Gly Ser Ser Gly Lys
1               5

<210> SEQ ID NO 111
<211> LENGTH: 7
<212> TYPE: PRT
<213> ORGANISM: Artifical
<220> FEATURE:
<223> OTHER INFORMATION: synthetic

<400> SEQUENCE: 111

Thr Arg Ser Ser Ser Gly Arg
1               5

<210> SEQ ID NO 112
<211> LENGTH: 7
<212> TYPE: PRT
<213> ORGANISM: Artificial
```

```
<220> FEATURE:
<223> OTHER INFORMATION: synthetic
<220> FEATURE:
<221> NAME/KEY: amino acidvariable
<222> LOCATION: (3)..(3)
<223> OTHER INFORMATION: X can be any codable amino acid residue
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: amino acidvariable
<222> LOCATION: (4)..(4)
<223> OTHER INFORMATION: X can be any codable amino acid residue
<220> FEATURE:
<221> NAME/KEY: amino acidvariable
<222> LOCATION: (5)..(5)
<223> OTHER INFORMATION: X can be any codable amino acid residue

<400> SEQUENCE: 112

Thr Arg Xaa Xaa Xaa Gly Arg
1               5

<210> SEQ ID NO 113
<211> LENGTH: 6
<212> TYPE: PRT
<213> ORGANISM: Artificial
<220> FEATURE:
<223> OTHER INFORMATION: synthetic

<400> SEQUENCE: 113

Leu Gly Ser Ser Gly Lys
1               5

<210> SEQ ID NO 114
<211> LENGTH: 6
<212> TYPE: PRT
<213> ORGANISM: Artificial
<220> FEATURE:
<223> OTHER INFORMATION: synthetic

<400> SEQUENCE: 114

Arg Gly Ser Ser Gly Lys
1               5

<210> SEQ ID NO 115
<211> LENGTH: 6
<212> TYPE: PRT
<213> ORGANISM: Artificial
<220> FEATURE:
<223> OTHER INFORMATION: synthetic

<400> SEQUENCE: 115

Gln Gly Ser Ser Gly Lys
1               5

<210> SEQ ID NO 116
<211> LENGTH: 6
<212> TYPE: PRT
<213> ORGANISM: Artificial
<220> FEATURE:
<223> OTHER INFORMATION: synthetic

<400> SEQUENCE: 116

Gly Gly Ser Ser Gly Lys
1               5

<210> SEQ ID NO 117
<211> LENGTH: 6
```

```
<212> TYPE: PRT
<213> ORGANISM: Artificial
<220> FEATURE:
<223> OTHER INFORMATION: synthetic

<400> SEQUENCE: 117

Ser Gly Ser Ser Gly Lys
1               5

<210> SEQ ID NO 118
<211> LENGTH: 7
<212> TYPE: PRT
<213> ORGANISM: Artificial
<220> FEATURE:
<223> OTHER INFORMATION: synthetic

<400> SEQUENCE: 118

Val Gly Ser Ser Asn Gly Lys
1               5

<210> SEQ ID NO 119
<211> LENGTH: 7
<212> TYPE: PRT
<213> ORGANISM: Artificial
<220> FEATURE:
<223> OTHER INFORMATION: synthetic

<400> SEQUENCE: 119

Val Gly Ser Ser Ala Gly Lys
1               5

<210> SEQ ID NO 120
<211> LENGTH: 7
<212> TYPE: PRT
<213> ORGANISM: Artificial
<220> FEATURE:
<223> OTHER INFORMATION: synthetic

<400> SEQUENCE: 120

Arg Gly Ser Ser Ser Gly Lys
1               5

<210> SEQ ID NO 121
<211> LENGTH: 11
<212> TYPE: PRT
<213> ORGANISM: Artificial
<220> FEATURE:
<223> OTHER INFORMATION: synthetic

<400> SEQUENCE: 121

Val Gly Leu Gly Gly Gly Pro Gly Lys Gly Arg
1               5                   10

<210> SEQ ID NO 122
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: X can be K, R, P, H, F, T, I, Q, W, A

<400> SEQUENCE: 122

Val Gly Ser Ser Ser Gly Xaa
1               5
```

```
<210> SEQ ID NO 123
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: G and A

<400> SEQUENCE: 123

Val Gly Ser Ser Ser Xaa Lys
1               5

<210> SEQ ID NO 124
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: X can be S,R,A,T,K,P,N,M,H,Q,V,G

<400> SEQUENCE: 124

Val Gly Ser Ser Xaa Gly Lys
1               5

<210> SEQ ID NO 125
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: R, A, Y, M, S, N, H, G

<400> SEQUENCE: 125

Val Gly Ser Xaa Ser Gly Lys
1               5

<210> SEQ ID NO 126
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: X can be L,Y,M,H,R,T,Q,K,V,S,A,G,P

<400> SEQUENCE: 126

Val Gly Xaa Ser Ser Gly Lys
1               5

<210> SEQ ID NO 127
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: X can be W,G,S,A,H,R,T,P
```

```
<400> SEQUENCE: 127

Val Xaa Ser Ser Ser Gly Lys
1               5

<210> SEQ ID NO 128
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X can be L,R,T,A,H,V,Q,G,S

<400> SEQUENCE: 128

Xaa Gly Ser Ser Ser Gly Lys
1               5

<210> SEQ ID NO 129
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X can be L, R, T, A, H, Q, G, S, V.
<220> FEATURE:
<221> NAME/KEY: MISC_FEATURE
<222> LOCATION: (2)..(2)
<223> OTHER INFORMATION: X can be W, G, S, A, H, R, and T
<220> FEATURE:
<221> NAME/KEY: MISC_FEATURE
<222> LOCATION: (3)..(3)
<223> OTHER INFORMATION: X can be L, Y, M, H, R, T, Q, K, V, S, A, G and
      P
<220> FEATURE:
<221> NAME/KEY: MISC_FEATURE
<222> LOCATION: (4)..(4)
<223> OTHER INFORMATION: X can be R, A, Y, M, S, N, H, and G
<220> FEATURE:
<221> NAME/KEY: MISC_FEATURE
<222> LOCATION: (5)..(5)
<223> OTHER INFORMATION: X can be  S, R, A, T, K P, N M, H, Q, V, and G
<220> FEATURE:
<221> NAME/KEY: MISC_FEATURE
<222> LOCATION: (6)..(6)
<223> OTHER INFORMATION: X can be  G and A
<220> FEATURE:
<221> NAME/KEY: MISC_FEATURE
<222> LOCATION: (7)..(7)
<223> OTHER INFORMATION: X can be K, R, P, H, F, T, I, Q, W, and A

<400> SEQUENCE: 129

Xaa Xaa Xaa Xaa Xaa Xaa Xaa
1               5

<210> SEQ ID NO 130
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<220> FEATURE:
<221> NAME/KEY: misc_feature
<222> LOCATION: (1)..(1)
<223> OTHER INFORMATION: Xaa can be any naturally occurring amino acid
```

```
<220> FEATURE:
<221> NAME/KEY: MISC_FEATURE
<222> LOCATION: (3)..(3)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<220> FEATURE:
<221> NAME/KEY: misc_feature
<222> LOCATION: (7)..(7)
<223> OTHER INFORMATION: Xaa can be any naturally occurring amino acid

<400> SEQUENCE: 130

Xaa Gly Xaa Gly Xaa Gly Xaa
1               5

<210> SEQ ID NO 131
<211> LENGTH: 4
<212> TYPE: PRT
<213> ORGANISM: Artificial
<220> FEATURE:
<223> OTHER INFORMATION: synthetic

<400> SEQUENCE: 131

Gly Ser Gly Lys
1

<210> SEQ ID NO 132
<211> LENGTH: 5
<212> TYPE: PRT
<213> ORGANISM: Artificial
<220> FEATURE:
<223> OTHER INFORMATION: synthetic

<400> SEQUENCE: 132

Ser Ser Ser Gly Lys
1               5

<210> SEQ ID NO 133
<211> LENGTH: 57
<212> TYPE: PRT
<213> ORGANISM: Artificial
<220> FEATURE:
<223> OTHER INFORMATION: synthetic

<400> SEQUENCE: 133

Phe Val Gln Gln His Leu Cys Gly Ser His Leu Val Glu Ala Leu Tyr
1               5                   10                  15

Leu Val Cys Gly Glu Arg Gly Phe Phe Tyr Thr Pro Arg Thr Gly Leu
                20                  25                  30

Gly Lys Gly Gln Gly Ile Val Glu Gln Cys Cys Thr Ser Ile Cys Ser
            35                  40                  45

Leu Tyr Gln Leu Glu Gln Tyr Cys Gly
        50                  55
```

```
<210> SEQ ID NO 134
<211> LENGTH: 56
<212> TYPE: PRT
<213> ORGANISM: Artificial
<220> FEATURE:
<223> OTHER INFORMATION: synthetic

<400> SEQUENCE: 134

Phe Val Asn Gln His Leu Cys Gly Ser His Leu Val Glu Ala Leu Tyr
1               5                   10                  15

Leu Val Cys Gly Glu Arg Gly Phe Phe Tyr Glu Pro Ala Thr Gly Leu
            20                  25                  30

Gly Lys Gln Gly Ile Val Glu Gln Cys Cys Thr Ser Ile Cys Ser Leu
        35                  40                  45

Tyr Gln Leu Glu Gln Tyr Cys Asn
    50                  55

<210> SEQ ID NO 135
<211> LENGTH: 57
<212> TYPE: PRT
<213> ORGANISM: Artificial
<220> FEATURE:
<223> OTHER INFORMATION: synthetic

<400> SEQUENCE: 135

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Ala Thr Gly Leu
            20                  25                  30

Gly Lys Gly Gln Gly Ile Val Glu Gln Cys Cys Thr Ser Ile Cys Ser
        35                  40                  45

Leu Tyr Gln Leu Glu Gln Tyr Cys Asn
    50                  55
```